United States Patent
Anderskewitz et al.

(10) Patent No.: US 6,407,130 B1
(45) Date of Patent: Jun. 18, 2002

(54) CARBOXAMIDE-SUBSTITUTED BENZIMIDAZOLES HAVING TRYPTASE-INHIBITING ACTIVITY

(75) Inventors: Ralf Anderskewitz, Bingen (DE); Christine Braun, Giubiasco (CH); Hans Briem, Ingelheim (DE); Bernd Disse, Mainz (DE); Christoph Hoenke, Ingelheim (DE); Hans Michael Jennewein, Wiesbaden (DE); Georg Speck, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/704,432

(22) Filed: Nov. 2, 2000

Related U.S. Application Data

(60) Provisional application No. 60/166,055, filed on Nov. 17, 1999.

(30) Foreign Application Priority Data

Nov. 10, 1999 (DE) .......................... 199 53 899

(51) Int. Cl.⁷ .................. A61K 31/4184; C07D 235/04
(52) U.S. Cl. ................. 514/394; 548/309.7; 548/306.1; 546/199; 546/273.4; 544/370; 514/253; 514/322; 514/338
(58) Field of Search ................. 514/394, 322, 514/338, 253, 370; 548/309.7, 306.1; 546/199, 273.4

(56) References Cited

U.S. PATENT DOCUMENTS 6,114,532 A * 9/2000 Ries et al. .................. 546/162

FOREIGN PATENT DOCUMENTS

| WO | WO 98/37075 A1 | 8/1998 |
| WO | WO 99 440072 A1 | 8/1999 |
| WO | WO 00 08014 A1 | 2/2000 |
| WO | WO 01 14342 A1 | 3/2001 |
| WO | WO 01 23359 A1 | 4/2001 |

OTHER PUBLICATIONS

Suzuki, N. et al; "Preparation of imidazole derivativesas gonadotropin–releasing hormone antagonists"; Chemical Abstracts, vol. 132, No. 20, May 15, 2000, Abstract No. 265201.

Kubo, K. et al; "Benzimidazole derivatives as neovascularization inhibitors and pharmaceutical compositions containing them"; Chemical Abstracts, vol. 133, No. 1, Jul. 3, 2000, Abstract No. 805.

* cited by examiner

*Primary Examiner*—Charanjit S. Aulakh
(74) *Attorney, Agent, or Firm*—Robert P. Raymond; Alan R. Stempel; Mary-Ellen M. Devlin

(57) ABSTRACT

The invention relates to carboxamide-substituted benzimidazole derivatives of general formula (I)

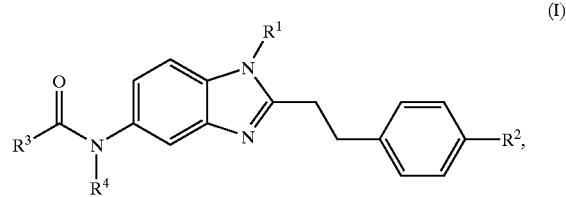

wherein the groups $R^1$, $R^2$, $R^3$ and $R^4$ may have the meanings given in the claims and in the specification, processes for preparing them and the use of carboxamide-substituted benzimidazole derivatives as pharmaceutical compositions, particularly as pharmaceutical compositions with a tryptase-inhibiting effect.

18 Claims, No Drawings

CARBOXAMIDE-SUBSTITUTED BENZIMIDAZOLES HAVING TRYPTASE-INHIBITING ACTIVITY

RELATED APPLICATIONS

Benefit of U.S. Provisional Application Serial No. 60/166,055, filed on Nov. 17, 1999 is hereby claimed.

FIELD OF THE INVENTION

The invention relates to carboxamide-substituted benzimidazole derivatives, methods of their manufacture, their use in the treatment of certain disease conditions, and pharmaceutical compositions comprising such compounds.

BACKGROUND TO THE INVENTION

Benzimidazole derivatives are known from the prior art as active substances with valuable pharmaceutical properties. Thus, International Patent Application WO 98/37075 discloses, in addition to other bicyclic heterocycles, benzimidazoles which can be effectively used to prevent and treat venous and arterial thrombotic diseases by virtue of their thrombin-inhibiting activity.

SUMMARY OF THE INVENTION

In contrast to the benzimidazole derivatives as described above and known from the prior art, which are useful for the treatment of thrombotic diseases, the present invention provides compounds having tryptase-inhibitory activity which can be used to prevent and treat inflammatory and/or allergic diseases.

DETAILED DESCRIPTION OF THE INVENTION

The present invention provides carboxamide-substituted benzimidazole derivatives of general formula (I)

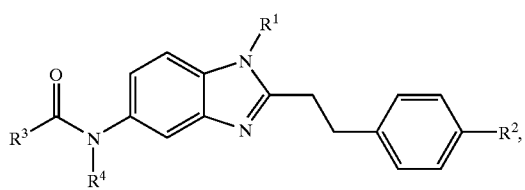

wherein
- $R^1$ denotes a group selected from among $C_1$–$C_6$-alkyl, $C_2$–$C_6$-alkenyl and $C_2$–$C_6$-alkynyl, which may optionally be mono-, di- or trisubstituted by one or more of the groups hydroxy, $C_1$–$C_4$-alkoxy, $CF_3$, phenoxy, COOH, halogen, —CO($C_1$–$C_4$-alkoxy), —CO—$NR^5R^6$, —$NR^5R^6$ or $C_1$–$C_4$-alkoxy-phenoxy, or
- phenyl-$C_1$–$C_4$-alkyl, which may optionally be mono-, di- or trisubstituted by one or more of the groups hydroxy, $C_1$–$C_4$-alkoxy, carboxy, halogen, $C_1$–$C_4$-alkoxycarbonyl or $CF_3$, or
- a 5- or 6-membered, saturated or unsaturated heterocycle linked directly or via a $C_1$–$C_4$-alkylene bridge, which may contain one or two heteroatoms selected from among oxygen, nitrogen or sulphur and which may optionally be substituted by $C_1$–$C_4$-alkyl or benzyl;
- $R^2$ denotes —C(=NH)$NH_2$ or —$CH_2$—$NH_2$;
- $R^3$ denotes a $C_1$–$C_6$-alkyl, $C_1$–$C_6$-hydroxyalkyl or $C_1$–$C_4$-alkoxy-$C_1$–$C_4$-alkyl group which may be mono- or disubstituted by one, two or three of the groups —$NR^5R^6$, —C(=NH)$NH_2$ or —NH—C(=NH)$NH_2$, or
- a 5-, 6- or 7-membered, saturated or unsaturated heterocycle linked directly or via a $C_1$–$C_4$-alkylene bridge or a $C_2$–$C_4$-alkenylene bridge, which may contain one, two or three heteroatoms selected from among oxygen, nitrogen or sulphur and which may optionally be mono- or disubstituted by hydroxy, $C_1$–$C_4$-alkyl, —COO—$C_1$–$C_4$-alkyl, —$CONH_2$, benzyl, diphenylmethyl, phenyl or pyridylmethyl, pyridyl, and wherein the phenyl substituent may be mono-, di- or trisubstituted by one or more groups selected from among $C_1$–$C_4$-alkyl, $C_1$–$C_4$-alkoxy, halogen, $C_1$–$C_4$-alkyl-halogen and —$NH_2$,
- cyclopropyl, cyclobutyl, cyclopentyl or cyclohexyl, each of which may be mono- or disubstituted by one or two of the groups —$NR^5R^6$, —C(=NH)$NH_2$ or —NH—C(=NH)$NH_2$, or phenyl-$C_1$–$C_4$-alkyl or naphthyl-$C_1$–$C_4$-alkyl, which may optionally be substituted at the alkylene bridge by —$NR^5R^6$ and may be mono- or disubstituted at the phenyl ring by one or two of the groups —$NO_2$, —$NR^5R^6$, —$C_1$–$C_4$-alkyl-$NR^5R^6$, —C(=NH)$NH_2$ or —NH—C(=NH)$NH_2$,
- $R^4$ denotes hydrogen or $C_1$–$C_6$-alkyl, which may optionally be mono- or disubstituted by one or two groups selected from among furanyl, benzofuranyl, thiophenyl, benzothiophenyl, anthracenyl, phenyl, pyridyl and naphthyl, while the substituents phenyl and naphthyl may in turn be mono-, di- or trisubstituted by one or more of the groups selected from among $C_1$–$C_4$-alkyl, $C_1$–$C_4$-alkoxy, halogen, $C_1$–$C_4$-alkyl-halogen, —$NH_2$, —NH($C_1$–$C_4$-alkyl), —N($C_1$–$C_4$-alkyl)$_2$, $NO_2$, hydroxy, —$CF_3$, —NHCO—$C_1$–$C_4$-alkyl, —COOH, —COO($C_1$–$C_4$-alkyl), —$CONH_2$, —CONH($C_1$–$C_4$-alkyl), —CON($C_1$–$C_4$-alkyl)$_2$, —CONH($C_1$–$C_4$-alkyl)—COO($C_1$–$C_4$-alkyl) and phenyl-$C_1$–$C_6$-alkyl;
- $R^5$ and $R^6$, which may be identical or different, denote hydrogen, $C_1$–$C_4$-alkyl, phenyl, pyridyl or benzyl, which may optionally be substituted by a group selected from among halogen, halo-$C_1$–$C_4$-alkyl, —OH, $C_1$–$C_4$-alkyl, —O—$C_1$–$C_4$-alkyl, —O—$C_1$–$C_4$-alkyl, —CO—O—$C_1$–$C_4$-alkyl, —$NO_2$, phenyl, pyrrolidin-1-yl, piperidin-1-yl, —$NH_2$, —NH—$C_1$–$C_4$-alkyl, —N($C_1$–$C_4$-alkyl)$_2$ and —C(=NH)$NH_2$—$NH_2$, optionally in the form of the tautomers, the racemates, the enantiomers, the diastereomers and the mixtures thereof, and optionally the pharmacologically acceptable acid addition salts thereof.

It has been found, surprisingly, that compounds of formula I have tryptase-inhibitory activity and that they may be used to treat disease conditions in which tryptase inhibitors have therapeutic value.

Preferred compounds according to the invention are the compounds of general formula (I),
wherein
- $R^1$ denotes $C_1$–$C_6$-alkyl, which may optionally be mono-, di- or trisubstituted by one or more of the groups hydroxy, $C_1$–$C_4$-alkoxy, $CF_3$, phenoxy, COOH, halogen, —CO($C_1$–$C_4$-alkoxy), —CO—$NR^5R^6$, —$NR^5R^6$ or $C_1$–$C_4$-alkoxy-phenoxy, or
- $R^2$ denotes —C(=NH)$NH_2$ or —$CH_2$—$NH_2$;
- $R^3$ denotes a $C_1$–$C_6$-alkyl group, which may be mono- or disubstituted by one or two of the groups —$NR^5R^6$, —C(=NH)$NH_2$ or —NH—C(=NH)$NH_2$, or a 5-, 6- or 7-membered, saturated or unsaturated heterocycle linked directly or via a $C_1$–$C_4$-alkylene bridge, which may contain one, two or three heteroatoms selected from among oxygen, nitrogen or sulphur and may optionally be mono- or disubstituted by hydroxy, $C_1$–$C_4$-alkyl, benzyl, phenyl or pyridyl, and wherein the phenyl substituent may be substituted by one of the groups selected from among $C_1$–$C_3$-alkyl, $C_1$–$C_3$-alkoxy, halogen, trifluoromethyl and $NH_2$, cyclopropyl, cyclopentyl or cyclohexyl, each of which may be mono- or disubstituted by one or two of the groups —$NR^5R^6$, —C(=NH)$NH_2$ or —NH—C(=NH)$NH_2$, or phenyl-$C_1$–$C_4$-alkyl or naphthyl-$C_1$–$C_4$-alkyl, which may optionally be substituted by —$NR^5R^6$ at the alkylene bridge and may be mono- or disubstituted at the phenyl ring by one or two of the groups —$NO_2$, —$NR^5R^6$, —$C_1$–$C_4$-Alkyl-$NR^5R^6$, —C(=NH)$NH_2$ or —NH—C(=NH)$NH_2$, $R^4$ denotes hydrogen or $C_1$–$C_6$-alkyl, which may optionally be mono- or disubstituted by one or two groups selected from among phenyl, pyridyl and naphthyl, wherein the substituents phenyl and naphthyl may in turn be substituted by one of the groups selected from among $C_1$–$C_4$-alkyl, $C_1$–$C_4$-alkoxy, halogen, —$C_1$–$C_4$-alkyl-halogen, —$NH_2$;

$R^5$ and $R^6$, which may be identical or different, denote hydrogen, $C_1$–$C_4$-alkyl, pyridyl or benzyl, which may optionally be substituted by a group selected from among —OH, —O—$C_1$–$C_3$-alkyl, —$NO_2$, phenyl, pyrrolidin-1-yl, —$NH_2$, —NH—$C_1$–$C_4$-alkyl, —N($C_1$–$C_4$-alkyl)$_2$ and —C(=NH)$NH_2$, optionally in the form of the tautomers, the racemates, the enantiomers, the diastereomers and the mixtures thereof, and optionally the pharmacologically acceptable acid addition salts thereof.

Also preferred are carboxamide-substituted benzimidazole derivatives of general formula (I), wherein $R^1$ denotes $C_1$–$C_4$-alkyl, which may optionally be mono-, di- or trisubstituted by one or more of the groups hydroxy, $C_1$–$C_4$-alkoxy, $CF_3$, phenoxy, COOH, halogen, —CO($C_1$–$C_4$-alkoxy), —CO—$NR^5R^6$, —$NR^5R^6$ or $C_1$–$C_4$-alkoxy-phenoxy, or $R^2$ denotes —C(=NH)$NH_2$ or —$CH_2$—$NH_2$;

$R^3$ denotes a $C_1$–$C_4$-alkyl group, which may be mono- or disubstituted by one or two of the groups —$NR^5R^6$, —C(=NH)$NH_2$ or —NH—C(=NH)$NH_2$, or a 5-, 6- or 7-membered, saturated or unsaturated heterocycle linked directly or via a methylene or ethylene bridge, which may contain one or two heteroatoms selected from among oxygen or nitrogen and may optionally be substituted by methyl or benzyl; naphthylmethyl, benzyl or phenylethyl, which may optionally be substituted by —$NR^5R^6$ at the alkylene bridge and may be substituted at the phenyl ring by a group selected from among —$NR^5R^6$, —$C_1$–$C_4$-alkyl-$NR^5R^6$, —C(=NH)$NH_2$ and —NH—C(=NH)$NH_2$, $R^4$ denotes hydrogen or $C_1$–$C_5$-alkyl, which may optionally be mono- or disubstituted by one or two groups selected from among pyridyl, phenyl and naphthyl;

$R^5$ and $R^6$, which may be identical or different, denote hydrogen, methyl, ethyl, propyl, butyl, pyridyl or benzyl, which may optionally be substituted by a group selected from among —OH, methoxy, —$NO_2$, phenyl, pyrrolidin-1-yl, —$NH_2$, —NH-methyl, —N(methyl)$_2$, —NH-ethyl, —N(ethyl)$_2$ and —C(=NH)$NH_2$, optionally in the form of the tautomers, the racemates, the enantiomers, the diastereomers and the mixtures thereof, and optionally the pharmacologically acceptable acid addition salts thereof.

Particularly preferred are carboxamide-substituted benzimidazole derivatives of general formula (I), wherein $R^1$ denotes methyl, ethyl, propyl or butyl, preferably methyl;

$R^2$ denotes —C(=NH)$NH_2$ or —$CH_2$—$NH_2$, preferably —C(=NH)$NH_2$;

$R^3$ denotes a $C_2$–$C_4$-alkyl group, which may be mono- or disubstituted by one or two of the groups —$NR^5R^6$, —C(=NH)$NH_2$ or —NH—C(=NH)$NH_2$, or a 6-membered, saturated or unsaturated heterocycle linked via a methylene or ethylene bridge, which contains one or two nitrogen atoms and may optionally be substituted by methyl or benzyl;

naphthylmethyl, benzyl or phenylethyl, which may optionally be substituted by —$NR^5R^6$ at the alkylene bridge and which are substituted at the phenyl ring by a group selected from among —$NR^5R^6$, —$C_1$–$C_4$-alkyl-$NR^5R^6$, —C(=NH)$NH_2$ and —NH—C(=NH)$NH_2$, $R^4$ denotes hydrogen or an alkyl group selected from among methyl, ethyl, propyl, butyl and pentyl, which may optionally be mono- or disubstituted by one or two groups selected from among pyridyl, phenyl and naphthyl;

$R^5$ and $R^6$, which may be identical or different, denote hydrogen, methyl, ethyl, propyl, butyl, pyridyl or benzyl, which may optionally be substituted by a group selected from among —OH, methoxy, —$NO_2$, phenyl, pyrrolidin-1-yl, —$NH_2$, —NH-methyl, —N(methyl)$_2$ and —C(=NH) $NH_2$, optionally in the form of the tautomers, the racemates, the enantiomers, the diastereomers and the mixtures thereof, and optionally the pharmacologically acceptable acid addition salts thereof.

Also particularly preferred are carboxamide-substituted benzimidazole derivatives of general formula (I), wherein $R^1$ denotes methyl, ethyl or propyl, preferably methyl;

$R^2$ denotes —C(=NH)$NH_2$ or —$CH_2$—$NH_2$, preferably —C(=NH)$NH_2$;

$R^3$ denotes methyl which is substituted by a group selected from among pyridylamino, benzylamino, N-benzyl-N-methylamino, N-(amidinobenzyl)amino, N-(amidinobenzyl)-N-methyl-amino, N-(dimethylaminobenzyl)amino, (pyrrolidin-1-ylbenzyl)amino and N-(dimethylaminobenzyl)-N-methyl-amino, or an alkyl group selected from among ethyl and propyl, which may be mono- or disubstituted by one or two groups selected from among —$NH_2$ and —NH—C(=NH)$NH_2$, or a heterocycle linked via an ethylene bridge, selected from among piperidine, morpholine and piperazine, which may optionally be substituted by methyl, benzyl or diphenylmethyl;

phenylethyl, which may optionally be substituted by —$NH_2$ at the ethylene bridge and is substituted at the phenyl ring by a group selected from among pyrrolidin-1-yl, —$NH_2$, —N(methyl)$_2$, —$CH_2$—$NH_2$ and —C(=NH)$NH_2$;

$R^4$ denotes hydrogen, methyl, ethyl, propyl, butyl, pentyl, benzyl, pyridylmethyl, naphthalinylmethyl or diphenylpropyl, optionally in the form of the tautomers, the racemates, the enantiomers, the diastereomers and the mixtures thereof, and optionally the pharmacologically acceptable acid addition salts thereof.

Of particular importance according to the invention are carboxamide-substituted benzimidazole derivatives of general formula (I), wherein $R^1$ denotes methyl, ethyl or propyl, preferably methyl;

$R^2$ denotes —C(=NH)NH$_2$ or —CH$_2$—NH$_2$, preferably —C(=NH)NH$_2$;

$R^3$ denotes methyl, which is substituted by a group selected from among N-(amidinobenzyl)amino, N-(amidinobenzyl)-N-methyl-amino, N-(dimethylaminobenzyl)amino, (pyrrolidin-1-ylbenzyl)amino and N-(dimethylaminobenzyl)-N-methyl-amino, or a piperidine linked via an ethylene bridge, which may optionally be substituted by benzyl;

phenylethyl, which may optionally be substituted by —NH$_2$ at the ethylene bridge and is substituted by —C(=NH)NH$_2$ at the phenyl ring;

$R^4$ may denote hydrogen, methyl, butyl, benzyl, naphthalinylmethyl or diphenylpropyl, optionally in the form of the tautomers, the racemates, the enantiomers, the diastereomers and the mixtures thereof, and optionally the pharmacologically acceptable acid addition salts thereof.

Particularly preferred are the compounds of general formula (IA)

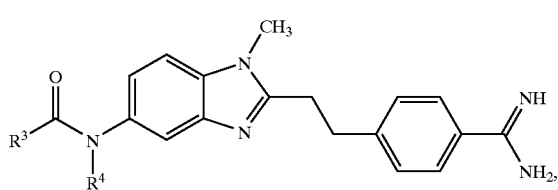

(IA)

wherein $R^3$ denotes methyl which is substituted by a group selected from among N-(amidinobenzyl)amino, N-(amidinobenzyl)-N-methyl-amino, N-(dimethylaminobenzyl)amino, (pyrrolidin-1-ylbenzyl)amino, and N-(dimethylaminobenzyl)-N-methyl-amino, or a piperidine or piperazine linked via an ethylene bridge, which may optionally be substituted by benzyl;

phenylethyl which may optionally be substituted by —NH$_2$ at the ethylene bridge and which is substituted at the phenyl ring by —C(=NH)NH$_2$;

$R^4$ denotes hydrogen, methyl, butyl, benzyl, naphthalinylmethyl or diphenylpropyl, optionally in the form of the tautomers, the racemates, the enantiomers, the diastereomers and the mixtures thereof, and optionally the pharmacologically acceptable acid addition salts thereof.

In addition to the abovementioned compounds of general formula (I) the present invention further relates to compounds which, because of a functionality which can be cleaved in vivo, are only converted into the therapeutically effective compounds of general formula (I) by the body after they have been taken by the patient. Such compounds are known as prodrugs. According to another aspect, therefore, the invention relates to prodrugs of general formula (II)

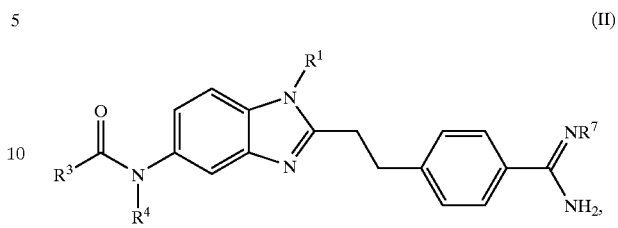

(II)

wherein $R^1$ and $R^4$ may have the meanings given hereinbefore and $R^3$ may be as hereinbefore defined or may denote $C_1$–$C_4$-alkyl, which is substituted by a group selected from among —C(=NOH)NH$_2$, —C(=NCOO—$C_1$–$C_{12}$-alkyl)NH$_2$ or —C(=NCOO—$C_1$–$C_8$-alkyl-phenyl)NH$_2$;

$R^7$ may denote hydroxy, —COO—$C_1$–$C_{12}$-alkyl, —CO-phenyl, —CO-pyridyl or —COO—$C_1$–$C_8$-alkyl-phenyl, whilst in the abovementioned group the phenyl ring may be substituted by $C_1$–$C_4$-alkyl, $C_1$–$C_4$-alkoxy, OH, halogen or $CF_3$, optionally in the form of the tautomers, the racemates, the enantiomers, the diastereomers and the mixtures thereof, and optionally the pharmacologically acceptable acid addition salts thereof.

Preferred are prodrugs of general formula (II), wherein $R^1$ and $R^4$ may be as hereinbefore defined and $R^3$ may have the meanings given above or denotes $C_1$–$C_4$-alkyl, which is substituted by a group selected from among —C(=NOH)NH$_2$, —C(=NCOO—$C_1$–$C_6$-alkyl)NH$_2$ or —C(=NCOO—$C_1$–$C_6$-alkyl-phenyl)NH$_2$;

$R^7$ may denote hydroxy, —COO—$C_1$–$C_6$-alkyl, —CO-phenyl, —CO-pyridyl or —COO—$C_1$–$C_6$-alkyl-phenyl, whilst in the abovementioned group the phenyl ring may be substituted by $C_1$–$C_4$-alkyl, $C_1$–$C_4$-alkoxy, OH, halogen or $CF_3$, optionally in the form of the tautomers, the racemates, the enantiomers, the diastereomers and the mixtures thereof, and optionally the pharmacologically acceptable acid addition salts thereof.

Particularly preferred are prodrugs of general formula (II), wherein $R^1$, $R^3$ and $R^4$ may be as hereinbefore defined and $R^7$ may denote hydroxy, methoxycarbonyl, ethoxycarbonyl, propyloxycarbonyl, butyloxycarbonyl, benzoyl, benzyloxycarbonyl or nicotinoyl, optionally in the form of the tautomers, the racemates, the enantiomers, the diastereomers and the mixtures thereof, and optionally the pharmacologically acceptable acid addition salts thereof.

The term alkyl groups (including those which are part of other groups) unless otherwise specified, denotes branched and unbranched alkyl groups having 1 to 12 carbon atoms, preferably 1 to 8 carbon atoms, most preferably having 1 to 6 carbon atoms. The following are mentioned by way of example: methyl, ethyl, propyl, butyl, pentyl, hexyl etc. Unless otherwise stated, the terms propyl, butyl, pentyl or hexyl given above also include all the possible isomeric forms. For example, the term propyl includes the two isomeric groups n-propyl and iso-propyl, the term butyl includes n-butyl, iso-butyl, sec. butyl and tert.-butyl, the term pentyl includes isopentyl, neopentyl etc. In some cases, common abbreviations will be used to denote the above-mentioned alkyl groups, such as Me for methyl, Et for ethyl etc.

Examples of alkenyl groups (including those which are part of other groups) are branched and unbranched alkenyl groups having 2 to 6 carbon atoms, preferably 2 to 4 carbon atoms, provided that they have at least one double bond, for example the abovementioned alkyl groups as well, provided that they have at least one double bond, such as, for example, vinyl (so long as no unstable enamines or enol ethers are formed), propenyl, iso-propenyl, butenyl, pentenyl, hexenyl.

It is also advantageous to use the compounds of general formula (I) as mentioned above for preparing a pharmaceutical composition for the prevention and/or treatment of fibroses such as lung fibrosis, fibrosing alveolitis and scarring, collagenoses such as lupus erythematodes and sclerodermia as well as arteriosclerosis, psoriasis and neoplasm.

The substituted benzimidazole derivatives of formula (I) and the prodrugs of general formula (II) may be synthesised by various methods. Possible approaches based on and using conventional methods of chemical synthesis are illustrated hereinafter by way of example. Diagram 1 shows a possible method of producing the basic benzimidazole structure of the compounds according to the invention.

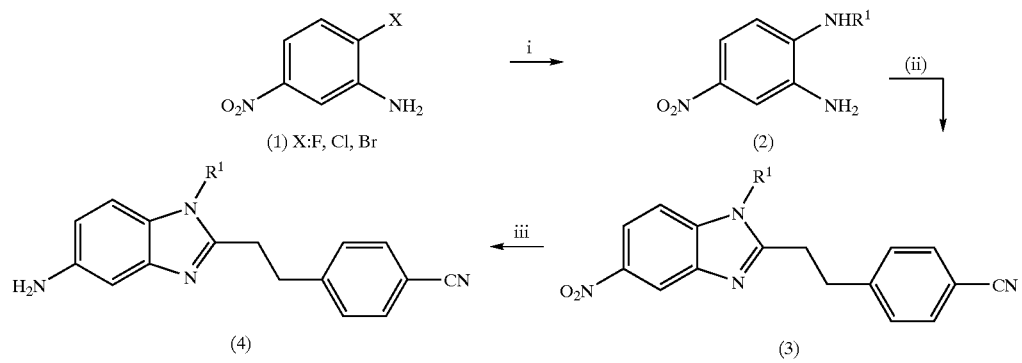

Examples of alkynyl groups (including those which are part of other groups) are alkynyl groups having 2 to 6 carbon atoms, provided that they have at least one triple bond, for example ethynyl, propargyl, butynyl, pentynyl, hexynyl.

The term halogen generally denotes fluorine, chlorine, bromine or iodine.

Examples of 5-, 6- or 7-membered, saturated or unsaturated heterocycles which may contain nitrogen, oxygen or sulphur as heteroatoms include for example furan, tetrahydrofuran, tetrahydrofuranone, γ-butyrolactone, α-pyran, γ-pyran, dioxolan, tetrahydropyran, dioxan, thiophene, dihydrothiophene, thiolan, dithiolan, pyrrole, pyrroline, pyrrolidine, pyrazole, pyrazoline, pyrazolidine, imidazole, imidazoline, imidazolidine, triazole, tetrazole, pyridine, piperidine, pyridazine, pyrimidine, pyrazine, piperazine, triazine, tetrazine, morpholine, thiomorpholine, diazepan, oxazole, isoxazole, oxazine, thiazole, isothiazole, thiadiazole, oxadiazole and pyrazolidine, unless otherwise specified in the definitions, whilst the heterocycle may be substituted as specified in the definitions.

"=O" denotes an oxygen atom linked via a double bond.

The present invention further relates to the use of the above-defined compounds of general formula (I) and of the prodrugs of general formula (II) for preparing a pharmaceutical composition for the treatment of diseases in which tryptase inhibitors may have a therapeutic value. It is preferred according to the invention to use the compounds of general formula I as described above, for preparing a pharmaceutical composition for the prevention and/or treatment of bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) and arthritis.

Diagram 1:

Starting from the 2-halo-5-nitro-anilines (1), aminolysis may be carried out first, to obtain the diaminonitrobenzenes (2) according to Diagram 1 (step i). The aminolysis of the compounds (1) with the primary amines $R^1$—$NH_2$ is carried out in suitable organic solvents such as for example dimethylsulphoxide, N,N-dimethylformamide, N-methylpyrrolidone, acetone or optionally in water or alcohols at ambient temperature or in a temperature range of 30–80° C., preferably 40–50° C.

The reaction of the compounds (2) with p-cyanophenylpropionic acid leads to the nitro-benzimidazoles (3, step ii) by reaction with p-cyanophenylpropionic acid in the presence of dehydrating reagents. The reaction is optionally carried out in a solvent or mixture of solvents such as methylene chloride, dimethylformamide, benzene, toluene, chlorobenzene, tetrahydrofuran, benzene/tetrahydrofuran or dioxan. Suitable dehydrating agents include for example isobutyl chloroformate, tetraethyl orthocarbonate, trimethyl orthoacetate, 2,2-dimethoxypropane, tetramethoxysilane, phosphorus oxychloride, thionylchloride, trimethylchlorosilan, phosphorus trichloride, phosphorus pentoxide, ethyl 1,2-dihydro-2-ethoxy-quinoline-1-carboxylate (EEDQ), 1,2-dihydro-2-i-propyloxy-quinoline-1-carboxylate (IIDQ), N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride. In some cases it may be beneficial to add a base such as pyridine, 4-dimethylaminopyridine, N-methyl-morpholine or triethylamine. The reaction is usually performed at temperatures between 0 and 150° C., preferably at temperatures between 20 and 120° C.

The nitrobenzimidazole derivatives (3) which may be obtained according to the procedure described above may be reductively converted into the amino-benzimidazoles (4) (step iii, Diagram 1). The reduction of the nitro group to form the compounds (3) is carried out for example by catalytic hydrogenation in organic solvents such as for example methanol, ethanol, isopropanol, tetrahydrofuran, optionally also in admixture with dimethylformamide, ethyl acetate, dioxan or acetic acid, at elevated hydrogen pressure or at normal pressure at temperatures between 0–50° C., preferably at 20–40° C. Suitable catalysts are the conventional hydrogenation catalysts. Palladium and Raney nickel are preferred. According to the invention, palladium is preferred. Palladium on charcoal (5%) is particularly preferred as catalyst. An alternative method of reducing the nitro compounds (3) envisages using reduction agents such as $Na_2S_2O_4$ or $SnCl_2$. This reaction is carried out in protic, water-miscible organic solvents such as short-chained alcohols (methanol, ethanol, isopropanol) or in a mixture of the abovementioned solvents with water, optionally with acetic acid, dimethylformamide or ethyl acetate. The reaction is usually carried out at elevated temperature, preferably at the reflux temperature of the solvent or mixture of solvents used. After all the starting compounds (3) have been converted working up is done in the usual way. The compounds (4) may be purified for example by crystallisation from non-polar organic solvents such as diethylether, petroleum ether, optionally mixed with ethyl acetate. Starting from the benzimidazoles (4) which may be obtained according to Diagram 1, the compounds (5) according to Diagram 2 are formed by reacting with the compounds $R^4$—Nu, where Nu denotes a nucleofugic leaving group such as for example chlorine, bromine, iodine, methanesulphonate, methyltriflate, p-toluenesulphonate etc. Alternatively, the compounds (5) may be obtained starting from the compounds (4) by reductive amination, by reacting with correspondingly substituted ketones or aldehydes under reductive conditions.

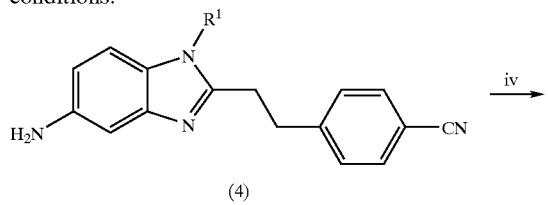

(4)

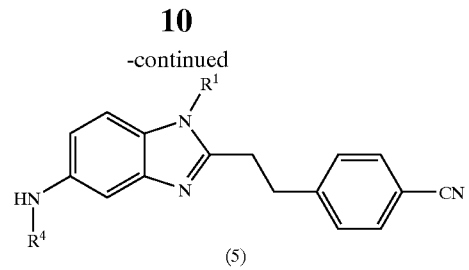

(5)

Diagram 2:

In order to react the compounds (4) with $R^4$—Nu according to step iv the following procedure may be used. A compound (4) is dissolved in a polar solvent, such as dimethylformamide, dimethylactamide, methylene chloride, tetrahydrofuran, preferably dimethylformamide and most preferably anhydrous, optionally absolute dimethylformamide. The solution thus obtained is mixed with a base and the corresponding alkylating agent R4—Nu. Suitable bases include the alkali metal- or alkaline earth metal carbonates of lithium, sodium, potassium and calcium such as sodium carbonate, lithium carbonate, potassium carbonate, calcium carbonate and preferably potassium carbonate. It is also possible to use the alkali metal- or alkaline earth metal hydroxides of lithium, sodium, potassium, magnesium, calcium, but preferably sodium hydroxide, potassium hydroxide, lithium hydroxide and calcium hydroxide in alcohol or water. The reaction mixture is stirred for 0.5–8 h, preferably 1–4 h at elevated temperature, preferably at 50–120° C., particularly at the reflux temperature of the solvent used. After conversion is complete the resulting mixture is worked up in the usual way and the crude product obtained is purified by crystallisation or chromatography on silica gel.

If the compounds (5) are obtained from the compounds (4) by reductive amination, the following method is used. The compound (4) is dissolved in a suitable solvent such as for example dichloromethane, dichloroethane, methanol, ethanol, tetrahydrofuran or toluene and between 0–60° C., preferably at 20–40° C. the corresponding carbonyl compound is added in the presence of an acid, preferably a carboxylic acid, most preferably a short-chained carboxylic acid, best of all acetic acid. Then a suitable reduction agent is added. Reduction agents which may be used according to the invention are $Na[HB(OAc)_3]$, $Na[BH_3CN]$, $NaBH_4$, $Pd/C—H_2$, preferably $Na[HB(OAc)_3]$. After working up in the conventional way, the product is purified by crystallisation or chromatography on silica gel.

The intermediates of general formula (III) may be obtained from the compounds (5), as shown in Diagram 3, by acylation (step v).

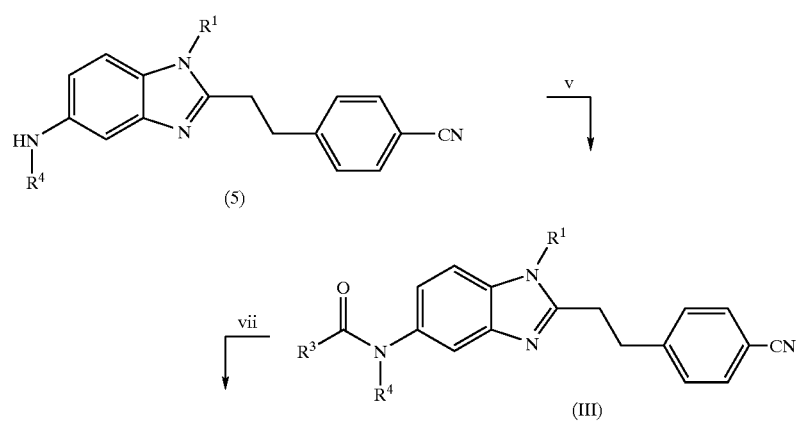

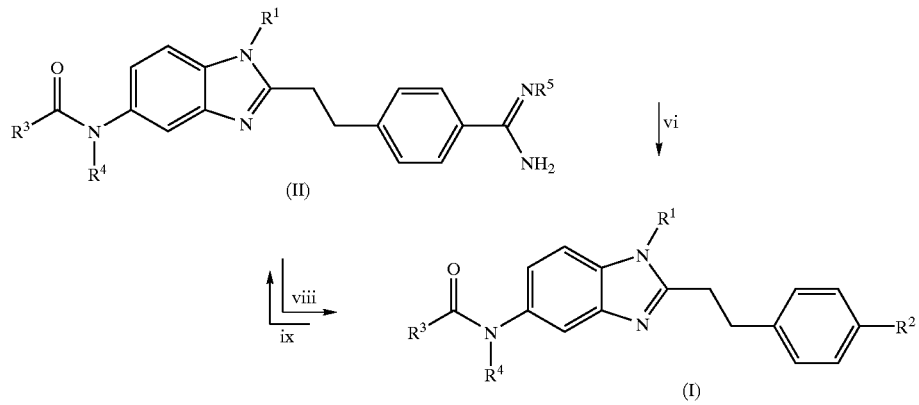

Diagram 3:

The reaction of the compounds (5) with the carboxylic acids $R^3$—COOH to obtain the intermediates of general formula (III) may be carried out in a solvent or mixture of solvents such as methylene chloride, dimethylformamide, benzene, toluene, chlorobenzene, tetrahydrofuran, benzene/tetrahydrofuran or dioxan, optionally in the presence of a dehydrating agent, e.g. in the presence of isobutyl chloroformate, tetraethyl orthocarbonates, trimethyl orthoacetate, 2,2-dimethoxypropane, tetramethoxysilan, thionylchloride, trimethylchlorosilan, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0 and 100° C. Alternatively the intermediates of general formula (III) may also be obtained by standard methods by reacting with correspondingly activated carboxylic acid derivatives $R^3$—COX (with X=halide, alkoxy, etc.) in the abovementioned solvents or mixtures of solvents in the presence of bases such as pyridine, 4-dimethylaminopyridine, N-methyl-morpholine or triethylamine.

According to step vi the compounds of general formula (I) according to the invention may be obtained from the intermediates (III). In order to prepare the compounds of general formula (I) according to the invention wherein $R^2$ denotes—C(=NH)NH$_2$, different methods may be used.

A compound of general formula (I) is obtained for example by treating a compound of general formula (III) with a corresponding alcohol such as methanol, ethanol, n-propanol, isopropanol or benzylalcohol, optionally mixed with another organic solvent such as for example chloroform, nitrobenzene or toluene in the presence of an acid such as hydrochloric acid or by reacting a corresponding amide with a trialkyloxonium salt such as triethyloxonium tetrafluoroborate in a solvent such as methylene chloride, tetrahydrofuran or dioxan at temperatures between −10 and 50° C., but preferably at 0–20° C. and subsequent aminolysis with alcoholic ammonia solution, for example. Alternatively, the compounds of general formula (I) may be obtained by reacting a compound of general formula (III) with sulphur nucleophils such as e.g. hydrogen sulphide, ammonium or sodium sulphide, sodium hydrogen sulphide, carbon disulphide, thioacetamide or bistrimethylsilylthioether, optionally in the presence of bases such as triethylamine, ammonia, sodium hydride or sodium alkoxide in solvents such as methanol, ethanol, water, tetrahydrofuran, pyridine, dimethylformamide or 1,3-dimethyl-imidazolidin-2-one at 20–100° C. and subsequently treating with a suitable methylating agent such as e.g. methyliodide or dimethylsulphate in a solvent such as acetonitrile or acetone at temperatures between −10 and 50° C., but preferably at 0–20° C. and subsequently treating with ammonia, ammonium carbonate or ammonium chloride in a suitable alcohol, such as for example methanol, ethanol, isopropanol etc. at temperatures between −10 and 50° C., but preferably at 0–20° C.

The compounds of general formula (I) according to the invention may also be obtained by treating a compound of general formula (III) with lithium hexamethyldisilazide in a suitable organic solvent such as e.g. tetrahydrofuran at temperatures between −20 and 50 ° C., but preferably at 0–20° C. and subsequently hydrolysing with dilute hydrochloric acid at 0–5° C. Another alternative method of obtaining compounds of general formula (I) comprises treating a compound of general formula (III) with ammonium chloride and trimethylaluminium in a suitable organic solvent such as e.g. toluene at temperatures between 20 and 150° C., but preferably at 110° C.

Compounds of general formula (I) wherein $R^2$ denotes —CH$_2$—NH$_2$ may be obtained from the intermediates (III) for example by catalytic hydrogenation on Raney nickel. These reactions are preferably carried out in protic organic solvents such as short-chained alcohols (methanol, ethanol or isopropanol) at temperatures between 10–40° C., preferably at 20–30° C. under normal pressure.

A compound of general formula (II) is obtained for example by treating a compound of general formula (III, Diagram 3, step vii) with hydroxylamine in the presence of carbonates or alkoxides of alkali or alkaline earth metals in solvents such as methanol, ethanol, n-propanol or isopropanol, optionally mixed with dioxan or tetrahydrofuran. The alkoxides may be prepared from the appropriate alkali metals or metal hydrides and the corresponding alcohol. The reaction is preferably carried out at 20–100° C., most preferably at the boiling temperature of the solvent used. Compounds of general formula (II) may alternatively be obtained by treating a compound of general formula (III) with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxan at temperatures between −10 and 50° C., but preferably at 0–20° C. and subsequently treating with hydroxylamine in the presence of bases in a suitable alcohol, such as methanol, ethanol, isopropanol etc. at temperatures between −10 and 50° C., but preferably at 0–20° C.

A compound of general formula (I) is obtained for example by treating a compound of general formula (II, Diagram 3, step viii) with hydrogen in the presence of hydrogenation catalysts such as Raney nickel or rhodium/aluminium oxide in water or methanol optionally with the addition of acids such as hydrochloric acid or methanesulphonic acid or by treating with hydrogen in the presence of palladium/charcoal in acetic acid/acetic anhydride at 20–50° C. and 1–5 bar hydrogen pressure, preferably at ambient temperature and normal pressure.

The acyl- or alkoxycarbonyl prodrugs (II) of the compound of general formula (I) are obtained by reacting the compounds of general formula (I) with the corresponding acid chlorides in the presence of bases such as e.g. triethylamine, N-methylmorpholine, diethylisopropylamine or DBU in a suitable solvent such as methylene chloride, chloroform, tetrahydrofuran, acetonitrile, dimethylformamide or dimethylsulphoxide.

In accordance with their central importance in the synthesis of the compounds of general formula (I) according to the invention and in the synthesis of the prodrugs of general formula (II), the invention relates in another aspect to the intermediates of general formula (III)

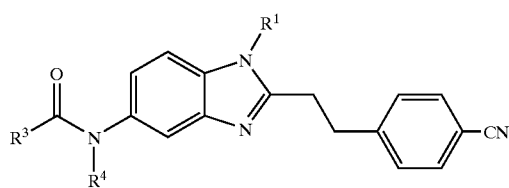

(III)

wherein the groups $R^1$, $R^3$ and $R^4$ may be as hereinbefore defined. The compounds of general formula (III) are valuable intermediate products for preparing the benzimidazole derivatives of general formula (I) according to the invention as well as the prodrugs of general formula (II) according to the invention.

By virtue of their pharmacological properties the compounds according to the invention may be used as pharmaceutical compositions, particularly as pharmaceutical compositions having a tryptase-inhibiting activity. They may be used in any circumstances where tryptase inhibitors may be of therapeutic benefit. It is preferred according to the invention to use compounds of formula (I) for preparing a pharmaceutical composition for the prevention and/or treatment of inflammatory and/or allergic diseases. It is particularly preferred to use compounds of general formula I as described above, for preparing a pharmaceutical composition for the prevention and/or treatment of bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) and arthritis.

It is also advantageous to use the compounds of general formula (I) as mentioned above for preparing a pharmaceutical composition for the prevention and/or treatment of fibroses such as lung fibrosis, fibrosing alveolitis and scarring, collagenoses such as lupus erythematodes and sclerodermia as well as arteriosclerosis, psoriasis and neoplasm.

Some procedures for preparing the compounds according to the invention will be described in more detail hereinafter by way of example. The following synthesis examples serve solely as a more detailed explanation, without restricting the object of the invention.

EXAMPLE 1

N-{2-[2-(4-Amidinophenyl)-ethyl]-1-methyl-benzimidazol-5-yl}-N-methyl-[3-(4-amidinophenyl)-propionamide]dihydrochloride

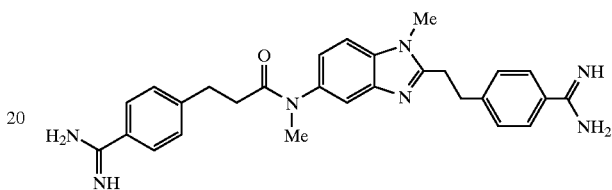

a) $N^1$-Methyl-1,2-diamino-4-nitrobenzene

2-Fluoro-5-nitro-aniline (15.0 g, 160 mmol) is taken up in 480 mL of 40% aqueous methylamine solution, stirred for 2.5 days at ambient temperature and for 2 h at 40–50° C. The mixture is diluted with water, the solid is filtered off, washed with water and dried. Yield: 26 g (97%); melting point: 171–173° C.

b) 2-[2-(4-Cyanophenyl)-ethyl]-1-methyl-5-nitro-benzimidazole $N^1$-methyl-1,2-diamino-4-nitrobenzene (8.3 g, 49.6 mmol) and p-cyano-phenylpropionic acid (9.6 g, 55 mmol) are taken up in 90 mL $POCl_3$, and refluxed for 1.5 h. After cooling the excess $POCl_3$ is decomposed with ice water. It is made alkaline with $NH_3$ with stirring/cooling and stirred for 1 h at ambient temperature. The solid is filtered off, washed with water and recrystallised from DMF.

Yield: 11.7 g (76.4%); melting point: 202–204° C.

c) 5-Amino-2-[2-(4-cyanophenyl)-ethyl]-1-methyl-benzimidazole

2-[2-(4-cyanophenyl)-ethyl]-1-methyl-5-nitro-benzimidazole (5.5 g, 18 mmol) in 150 mL THF/75 mL methanol is hydrogenated in the presence of 1.0 g 5% Pd/C at ambient temperature and normal pressure. The catalyst is filtered off, the filtrate is evaporated down until not quite dry, diluted with 100 mL acetonitrile and evaporated down to a residual volume of 30 mL. The crystal slurry is cooled and filtered. The crystals are washed with cold acetonitrile and ether.

Yield: 4.7 g (94%); melting point: 187–192° C.

d) N-{2-[2-(4-Cyanophenyl)-ethyl]-1-methyl-benzimidazol-5-yl}-trifluoroacetamide 2.2 mL of trifluoroacetic acid anhydride are added dropwise to 4.1 g (15 mmol) of 5-amino-2-[2-(4-cyanophenyl)-ethyl]-1-methyl-benzimidazole in 40 mL of pyridine at 5–20° C. The mixture is stirred for 15 min. at ambient temperature and diluted with water. The solid is filtered off and washed with water. The crystals are dissolved in 300 mL ethyl acetate with heating, dried and evaporated down until not quite dry. The residue is cooled, the solid precipitated is filtered off and washed with diethylether.

Yield: 4.1 g (74%); melting point: 225–228° C.
e) 2-[2-(4-Cyanophenyl)-ethyl]-1-methyl-5-methylamino-benzimidazole 4.1 g (11 mmol) of N-{2-[2-(4-cyanophenyl)-ethyl]-1-methyl-benzimidazol-5-yl}-trifluoroacetamide are cooled to about 10° C. in 20 mL dimethylsulphoxide and 80% NaH (0.33 g, about 11 mmol) are added in batches with stirring. The mixture is heated to 40–50° C. for 0.5 h and then cooled to 30° C. Methyl iodide (0.75 mL, 11.9 mmol) is then added dropwise. The mixture is stirred for 0.5 h at 40–50° C., diluted with 100 mL ethyl acetate, poured onto water and extracted. The organic phase is again washed with water, dried and evaporated down. The residue is chromatographed over silica gel. The methylated trifluoroacetamide is taken up in MeOH, combined with 10 mL of conc. aqueous ammonia solution and stirred for 4 h at 30–40° C. The methanol is distilled off, the residue is taken up in 75 mL of ethyl acetate, washed with water, dried and evaporated down. The product is crystallised from diethylether. Yield: 2.0 g (63%); melting point: 155–158° C.

f) N-{2-[2-(4-Cyanophenyl)-ethyl]-1-methyl-benzimidazol-5-yl}-N-methyl-[3-(4-cyanophenyl)-propionamide]

2-[2-(4-cyanophenyl)-ethyl]-1-methyl-5-methylamino-benzimidazole (0.9 g, 3.1 mmol), 3-(p-cyanophenyl)-propionic acid (0.6 g, 3,4 mmol) and 0.5 mL of N-methylmorpholine are taken up in 10 mL of dimethylformamide. TBTU (1.2 g, 3.7 mmol) is added and the mixture is stirred for 16 h at ambient temperature. After dilution with 75 mL of ethyl acetate the mixture is washed with dilute aqueous NaOH or saturated NaHCO$_3$ solution and with water, dried and evaporated down. The product is crystallised from ethyl acetate/diethylether.

Yield: 1.3 g (94%); melting point: 138–140° C.

g) N-{2-[2-(4-Amidinophenyl)-ethyl]-1-methyl-benzimidazol-5-yl}-N-methyl-[3-(4-amidinophenyl)-propionamide]-dihydrochloride N-{2-[2-(4-cyanophenyl)-ethyl]-1-methyl-benzimidazol-5-yl}-N-methyl-[3-(4-cyanophenyl)-propionamide] (1.3 g, 2.9 mmol) is taken up in 50 mL of a saturated ethanolic HCl solution cooled to 0° C. The mixture is stirred until the educt is fully dissolved and then kept overnight at 0–5° C. The ethanol is distilled off at a maximum of 40° C. and the residue is taken up in 40 mL of a saturated ethanolic ammonia at 0° C. This is stirred for 2 h at ambient temperature, then for 3 h at 50–60°, combined with a further 10 mL of saturated ammonia solution, refluxed for 2 h and kept overnight at ambient temperature. The inorganic salts precipitated are filtered off, the filtrate is evaporated down and the residue is chromatographed over silica gel.

Yield: 1.0 g (62%); Mass: calculated: [481], found: [M+H]$^+$ 482. $^1$H-NMR (250 MHz,CD$_3$OD): δ=7.86–7.06 (11H,m,aryl-H); 3.81 (3H,s,N—CH$_3$); 3.3 (4H;s; —CH$_2$—CH$_2$—); 3.29 (3H,s,O=C—N—CH$_3$); 3.02; 2.46 (4H, 2t,J= 7.6 Hz, O=C—CH$_2$CH$_2$—).

EXAMPLE 2

N-{2-[2-(4-Amidinophenyl)-ethyl]-1-methyl-benzimidazol-5-yl}-N-methyl-[3-(N-benzyl-piperid-4-yl)-propionamide]-dihydrochloride

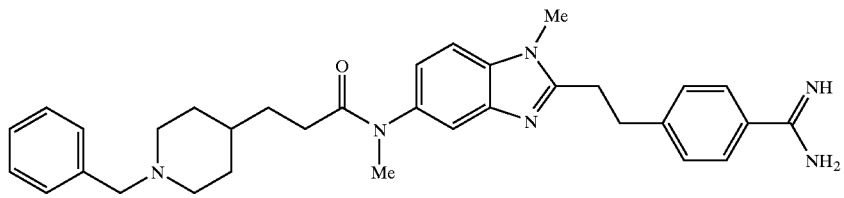

The synthesis starts with the 2-[2-(4-cyanophenyl)-ethyl]-1-methyl-5-methylamino-benzimidazole (2.4 mmol) obtainable according to Example 1, step e, and 3-(N-benzyl-piperid-4-yl)-propionic acid by coupling with TBTU analogously to the method described in Example 1, step f. The title compound obtained according to Example 1, step g is purified by chromatography on silica gel. Yield: 61%; Mass: calculated: [536], found: [M+H]$^+$ 537, [M+2H]$^{2+}$0 269. $^1$H-NMR (250 MHz, CD$_3$OD): δ=7.98–7.34 (12H, m, aryl-H); 4.20 (2H, s, N—CH$_2$); 3.97 (3H, s, N—CH$_3$); 3.61; 3.36 (4H, 2m,—CH$_2$—CH$_2$—); 3.05–1.20 (13H, m, piperidinylethyl); 3.32 (3H, s, O=C—N—CH$_3$).

EXAMPLE 3

N-{2-[2-(4-Amidinophenyl)-ethyl]-1-benzyl-benzimidazol-5-yl}-N-methyl-[3-(N-benzyl-piperid-4-yl)-propionamide]-dihydrochloride

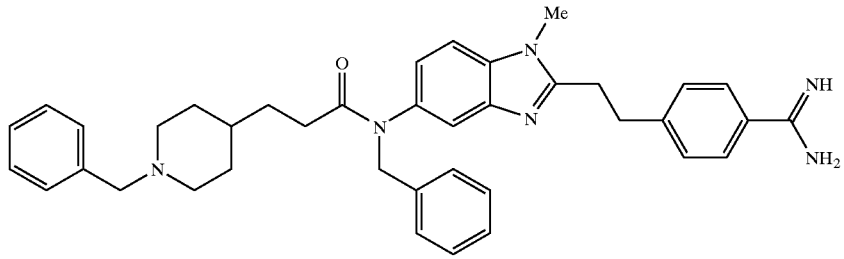

The synthesis is carried out analogously to the method described for Example 2. The title compound is purified by chromatography on silica gel. Yield: 53%.

Mass: calculated: [612], found: [M+H]+ 613, [M+2H]2+ 307. 1H-NMR (250 MHz, CD3OD):δ=7.97–7.21 (17H, m, aryl-H); 5.04; 4.32 (4H, 2s, N—CH2-Ph); 3.94 (3H, s, N—CH3); 3.44; 2.97 (4H, 2m, —CH2—CH2); 3.48–1.22 (13H, m, piperidinylethyl).

EXAMPLE 4

N-{2-[2-(4-Amidinophenyl)-ethyl]-1-methyl-benzimidazol-5-yl}-[2-amino-3-(p-amidinophenyl)-propionic Acid Amide]-trihydrochloride

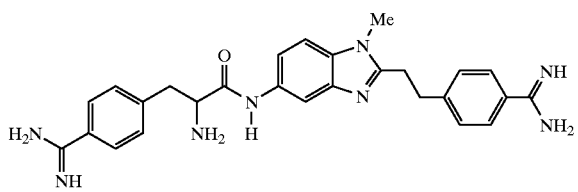

a) N-{2-[2-(4-Cyanophenyl)-ethyl]-1-methyl-benzimidazol-5-yl}-[3-(p-cyanophenyl)-2-t-butyloxycarbonylamino-propionic Acid Amide]

The synthesis is carried out starting from 10 mmol of 5-amino-2-[2-(4-cyanophenyl)-ethyl]-1-methyl-benzimidazole (Example 1, step d) and Boc-p-cyano-phenylalanine analogously to the method described for Example 1, step f.

Yield: 93%;

b) N-{2-[2-(4-Amidinophenyl)-ethyl]-1-methyl-benzimidazol-5-yl}-[2-amino-3-(p-amidinophenyl)-propionic Acid Amide]-trihydrochloride The title compound is synthesised as described for Example 1, step g, starting from N-{2-[2-(4-cyanophenyl)-ethyl]-1-methyl-benzimidazol-5-yl}-[3-(p-cyanophenyl)-2-t-butyloxycarbonylamino-propionic acid amide].

Melting point: >260° C.; Mass: calculated: [482], found: [M+H]+ 483, [M+2H]2+ 242. 1H-NMR (25 OMHz,DMSO-d6); 11.93 (1H,s,NH—C); 9.63; 9.32 (8H,2s, —C(=NH2+)NH2) 8.72 (3H,s,NH3+); 7.82–7.55 (11H,m,aryl-H); 4.58 (1H,m, —CH—CH2); 3,94 (3H,s,N—CH3); 6H,m, —CH—CH2—;CH2—CH2—).

EXAMPLE 5

N-{2-[2-(4-Amidinophenyl)-ethyl]-1-methyl-benzimidazol-5-yl}-N-isobutyl-[3-(4-amidinophenyl)-propionamide]-dihydrochloride

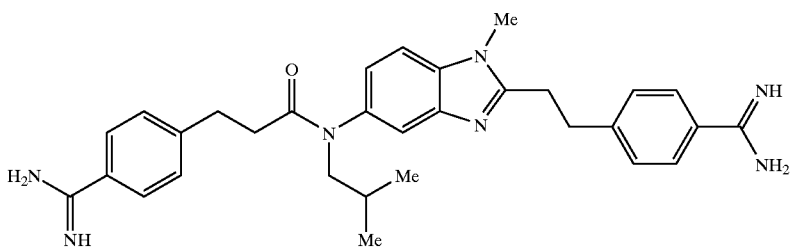

a) 2-[2-(4-Cyanophenyl-ethyl]-1-methyl-5-isobutylamino-benzimidazole 1.0 g (3.6 mmol) of 5-amino-2-[2-(4-cyanophenyl)-ethyl]-1-methyl-benzimidazole (obtainable according to Example 1, step c) and isobutyraldehyde (0.33 mL, 3.6 mmol) in 25 mL dichloromethane are mixed with 0.22 mL of acetic acid at ambient temperature and with Na[HB(OAc)3] with stirring. The mixture is stirred for 1 h at ambient temperature, covered with water, carefully acidified with concentrated aqueous hydrochloric acid and then made alkaline with 4N NaOH solution. The organic phase is separated off, dried and evaporated down. The product is chromatographed over silica gel and optionally crystallised from diethylether.

Yield: 0.8 g (67%); melting point: 112–114° C.

b) N-{2-[2-(4-Cyanophenyl)-ethyl]-1-methyl-benzimidazol-5-yl}-N-isobutyl-[3-(4-cyanophenyl)-propionamide]

3-(p-cyanophenyl)-propionic acid (0.69 g, 3.9 mmol) in 15 mL chloroform is combined with 1.3 mL of thionyl chloride and refluxed for 3 h. The solvent and the excess thionyl chloride are distilled off, the residue is dissolved in 10 mL of dichloromethane and added dropwise to a solution of 2-[2-(4-cyanophenyl)-ethyl]-1-methyl-5-isobutylamino-benzimidazole (1.25 g, 3.8 mmol) and 1.3 mL N-methylmorpholine in 50 mL dichloromethane. This is refluxed for 0.5 h, cooled, mixed with water and extracted into the organic phase. It is washed with dilute, aqueous NaOH and with water, dried and evaporated down. The product is further reacted without being purified.

c) N-{2-[2-(4-Amidinophenyl)-ethyl]-1-methyl-benzimidazol-5-yl}-N-isobutyl-[3-(4-amidinophenyl)-propionamide]-dihydrochloride N-{2-[2-(4-cyanophenyl)-ethyl]-1-methyl-benzimidazol-5-yl}-N-isobutyl-[3-(4-cyanophenyl)-propionamide] (crude product obtained according to step b) is taken up in 25 mL of a cooled ethanolic HCl solution saturated at 0° C. This is stirred until the educt is completely dissolved and then kept overnight at 0–5° C. The ethanol is distilled off at a maximum temperature of 40° C. and the residue is taken up in 30 mL of an ethanolic ammonia solution saturated at 0° C. This is stirred for 1 h at ambient temperature, for 2 h at 40–50° C., a further 10 mL of saturated ammonia solution are added, the mixture is refluxed for 1 h and kept at ambient temperature overnight. The alcohol is distilled off, the residue is suspended in dichloromethane/methanol=4/1, the insoluble inorganic residue is filtered off and the filtrate is chromatographed over silica gel. The product is crystallised from ethanol/acetone with a little water.

Yield: 1.5 g (66%); melting point: >220° C.; Mass: calculated: [523], found: [M+H]+ 524, [M+Na]+ 546 1H-NMR (250 MHz, CD3OD):δ=7.88–6.99 (11H, m, aryl-H); 3.78 (3H, s, N—CH3); 3.58 (2H, d, J=7.4 Hz, CH2—CH); 3.36 (4H, s, —CH2—CH2—); 2.98; 2.42 (4H, 2t, J=7.6 Hz, O=C—CH2CH2—); 1.72 (1H, m, CH—(CH3)2); 0.88 (6H, d, J=6.4 Hz, (CH3)2—CH).

EXAMPLE 6

N-{2-[2-(4-Amidinophenyl)-ethyl]-1-methyl-benzimidazol-5-yl}-N-methyl-[3-(piperid-4-yl)-propionamide]-dihydrochloride

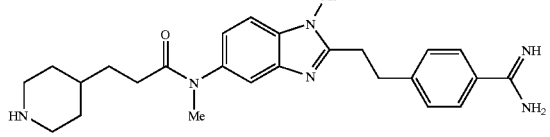

0.8 g (1.3 mmol) of N-{2-[2-(4-amidinophenyl)-ethyl]-1-methyl-benzimidazol-5-yl}-N-methyl-[3-(N-benzyl-piperid-4-yl)-propionamide] (Example 2) are hydrogenated in 50 mL of methanol in the presence of 5% Pd/C at normal pressure and 40–50° C. The catalyst is filtered off and the filtrate is evaporated down.

Yield: 0.7 g (about 100%); Mass: calculated: [446], found: [M+H]$^+$ 447. $^1$H-NMR (250 MHz, CD$_3$OD):δ= 7.97–7.47 (7H, m, aryl-H); 3.98 (3H, s, N—CH$_3$) 3.62; 3.36 (4H, 2m, —CH$_2$—CH$_2$—); 3.34 (3H,s, O=C—N—CH$_3$); 2,88–1.09 (13H, m, piperidinylethyl).

EXAMPLE 7

N-{2-[2-(4-Amidinophenyl)-ethyl]-1-methyl-benzimidazol-5-yl}-N-methyl-[3-(piperid-4-yl)-propionamide]-dihydrochloride

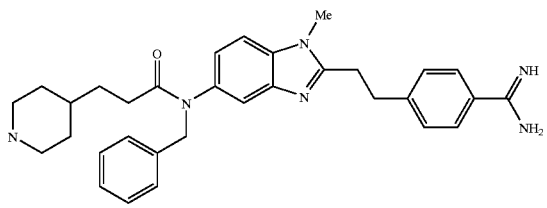

2.4 mmol of N-{2-[2-(4-amidinophenyl)-ethyl]-1-benzyl-benzimidazol-5-yl}-N-methyl-[3-(N-benzyl-piperid-4-yl)-propionamide] (Example 3) are reacted analogously to the method described for Example 6 to obtain the title compound.

Yield: 80%; Mass: calculated: [522], found: [M+H]$^+$ 523, [M+2H]$^{2+}$ 262. $^1$H-NMR (250 MHz, CD$_3$OD): δ=7.94–7.16 (12H, m, aryl-H); 5.02 (2H, s, N—CH$_2$); 3.97 (3H, s, N—CH$_3$); 3.78; 3.24 (4H, 2m, —CH$_2$—CH$_2$—); 2.90–1.13 (13H, m, piperidinylethyl).

EXAMPLE 8

N-{2-[2-(4-Amidinophenyl)-ethyl]-1-methylbenzimidazol-5-yl}-N-(α-naphthylmethyl)-[3-amidinobenzylaminoacetamide]-trihydrochloride

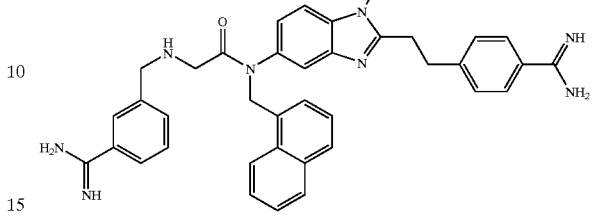

2-[2-(4-Cyanophenyl)-ethyl]-1-methyl-5-(α-naphthylmethyl)-benzimidazole

5-Amino-2-[2-(4-cyanophenyl)-ethyl]-1-methyl-benzimidazole (35.5 g, 129.0 mmol) (obtainable according to Example 1, Step c) and 18.2 ml of naphthaline-1-carbaldehyde are reacted by reductive amination according to Example 5, Step a.

Yield: 48.0 g (89%);

b) N-{2-[2-(4-Cyanophenyl)-ethyl]-1-methyl-benzimidazol-5-yl}-N-(α-naphthylmethyl)-[2-(N-tertbutyloxycarbonyl)-amine]-acetic Acid Amide Synthesis is carried out starting from 3.7 g (8.9 mmol) of 2-[2-(4-cyanophenyl)-ethyl]-1-methyl-5-(α-naphthylmethylamino)-benzimidazole and 2.3 g (13.3 mmol) of boc-glycine analogously to the method described for Example 1, Step f.

Yield: 4.0 g (80%).

c) N-{2-[2-(4-Cyanophenyl)-ethyl]-1-methylbenzimidazol-5-yl}-N-(α-naphthylmethyl)-2-(3-cyanobenzylamine)-acetic Acid Amide 2.7 g (5.7 mmol) of N-{2-[2-(4-cyanophenyl)-ethyl]-1-methyl-benzimidazol-5-yl}-N-(α-naphthylmethyl)-2-aminoacetic acid amide are reacted by reductive amination according to Example 1, Step c with 0.82 g (6.3 mmol) of 3-cyanobenzaldehyde to obtain the title compound.

Yield: 2.6 g (88%).

d) N-{2-[2-(4-Amidinophenyl)-ethyl]-1-methylbenzimidazol-5-yl}-N-(α-naphthylmethyl)-[3-amidinobenzylaminoacetamide]-trihydrochloride 1.3 g (2.2 mmol) of N-{2-[2-(4-cyanophenyl)-ethyl]-1-methyl-benzimidazol-5-yl}-N-(α-naphthylmethyl)-2-(3-cyanobenzylamine)-acetic acid amide were reacted according to Example 1, Step g.

Yield: 1.0 g (54%). Mass: calc.: [622], found: [M+H]$^+$ 623. $^1$H-NMR (250 MHz, DMSO-d6): δ=9.80 (1H, s, NH); 9.52 (1H, s, amidine); 9.44 (1H, s, amidine); 9.36 (1H, s, amidine); 9.23 (1H, s, amidine); 8.29–7.11 (18H, m, aryl-H); 6.50 (2H, s, CH$_2$); 4.24 (2H, s, CH$_2$); 3.86 (3H, s, CH$_3$); 3.67 (2H, s, CH$_2$); 3.46–3.23 (4H, m, CH$_2$—CH$_2$).

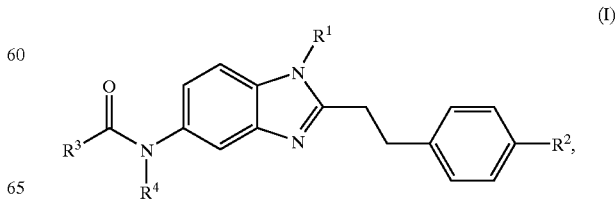

(I)

TABLE 1

| No | -R¹ | -R² | -R³ | -R⁴ | Chemical name |
|---|---|---|---|---|---|
| 9 | -Methyl | amidine (C(=NH)NH₂) | -CH₂CH₂-C₆H₄-C(=NH)NH₂ (para) | 1-ethyl-naphthalen-? (naphthylmethyl with ethyl) | N-{2-[2-(4-Amidinophenyl)-ethyl]-1-methy-benzimidazol-5-yl}-N-β-naphthylmethyl-[3-(4-amidinophenyl)-propionamide]-dihydrochloride |
| 10 | -Methyl | amidine | -CH₂CH₂-C₆H₄-C(=NH)NH₂ | -CH₂CH₂CH(Ph)(Ph) | N-{2-[2-(4-Amidinophenyl)-ethyl]-1-methyl-benzimidazol-5-yl}-N-(3,3-diphenylpropyl)-[3-(4-amidinophenyl)-propionamide]-dihydrochloride |
| 11 | -Methyl | amidine | -CH₂CH₂-C₆H₄-C(=NH)NH₂ | 6-ethyl-naphthalen-2-ylmethyl | N-{2-[2-(4-Amidinophenyl)-ethyl]-1-methyl-benzimidazol-5-yl}-N-β-naphthylmethyl-[3-(4-amidinophenyl)-propionamide]-dihydrochloride |
| 12 | -Methyl | amidine | -CH₂CH₂-C₆H₄-C(=NH)NH₂ | -Benzyl | N-{2-[2-(4-Amidinophenyl)-ethyl]-1-methyl-benzimidazol-5-yl}-N-benzyl-[3-(4-amidinophenyl)-propionamide]-dihydrochloride |
| 13 | -Methyl | amidine | -CH(NH₂)CH₂CH₂CH₂-NH-C(=NH)NH₂ | hydrogen | N-{2-[2-(4-Amidinophenyl)-ethyl]-1-methyl-benzimidazol-5-yl}-[2-amino-5-guanidino-pentanoic acid amide]-trihydrochloride |
| 14 | -Methyl | amidine | -CH(NH₂)CH₂-C₆H₄-CH₂NH₂ | hydrogen | N-{2-[2-(4-Amidinophenyl)-ethyl]-1-methyl-benzimidazol-5-yl}-[2-amino-3-[p-(aminomethyl)-phenyl]-propionic acid amide]-trihydrochloride |
| 15 | -Methyl | amidine | -CH₂-NH-(pyridin-3-yl) | -Methyl | N-{2-[2-(4-Amidinophenyl)-ethyl]-1-methyl-benzimidazol-5-yl}-N-methyl-[2-(pyrid-2-ylamino)-acetamid]-hydrochloride |
| 16 | -Methyl | amidine | -CH₂CH₂-C₆H₄-C(=NH)NH₂ | -CH₂CH₂CH(Me)Me (isopentyl) | N-{2-[2-(4-Amidinophenyl)-ethyl]-1-methyl-benzimidazol-5-yl}-N-isopentyl-[3-(4-amidinophenyl)-propionamide]-dihydrochloride |
| 17 | -Methyl | amidine | -CH(NH₂)CH₂CH₂CH₂-NH₂ | hydrogen | N-{2-[2-(4-Amidinophenyl)-ethyl]-1-methyl-benzimidazol-5-yl}-[2,5-diamino-pentanoic acid amide]-trihydrochloride |
| 18 | -Methyl | amidine | 3-(N-methyl-N-ethyl-aminomethyl)-benzamidine | 1-ethyl-naphthyl | N-{2-[2-(4-Amidinophenyl)-ethyl-1-methyl-benzimidazol-5-yl}-N-(-naphthylmethylamino)-N-methyl-N-[3-amidinobenzyl]-acetamide-trihydrochloride |
| 19 | -Methyl | amidine | -CH₂CH₂-C₆H₄(3-)-C(=NH)NH₂ | 1-ethyl-naphthyl | N-{2-[2-(4-Amidinophenyl)-ethyl]-1-methyl-benzimidazol-5-yl}-N--naphthylmethyl-[3-(3-amidinophenyl)-propionamide]-dihydrochloride |

TABLE 1-continued

| No | -R¹ | -R² | -R³ | -R⁴ | Chemical name |
|----|-----|-----|-----|-----|---------------|
| 20 | -Methyl | 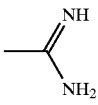 | 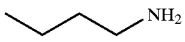 | 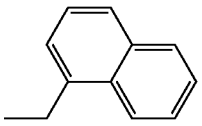 | N-{2-[2-(4-Amidinophenyl)-ethyl]-1-methyl-benzimidazol-5-yl}-N--naphthylmethyl-[4-amino-butanoic acid amide]-dihydrochloride |
| 21 | -Methyl | 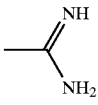 | 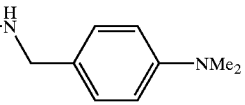 | 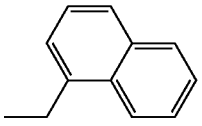 | N-{2-[2-(4-Amidinophenyl)-ethyl]-1-methyl-benzimidazol-5-yl}-N-( -naphthyl)-[4-dimethylaminobenzylamino-acetamide]-dihydrochloride |
| 22 | -Methyl | 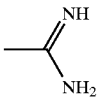 | 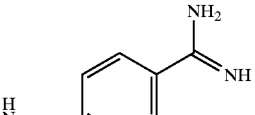 | 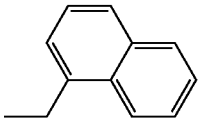 | N-{2-[2-(4-Amidinophenyl)-ethyl]-1-methyl-benzimidazol-5-yl}-N-( -naphthylmethyl)-[4-amidinobenzylamino-acetamide]-trihydrochloride |
| 23 | -Methyl | 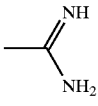 | 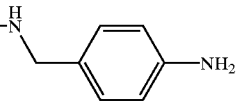 | 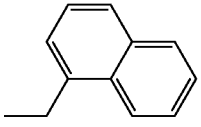 | N-{2-[2-(4-Amidinophenyl)-ethyl]-1-methyl-benzimidazol-5-yl}-N-( -naphthylmethyl)-[4-aminobenzylamino-acetamide]-trihydrochloride |
| 24 | -Methyl | 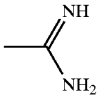 | 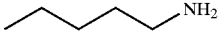 | 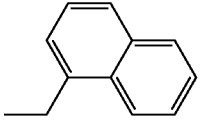 | N-{2-[2-(4-Amidinophenyl)-ethyl]-1-methyl-benzimidazol-5-yl}-N-( -naphthylmethyl)-[5-amino-pentanoic acid amide]-dihydrochloride |
| 25 | -Methyl | 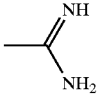 | 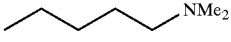 | 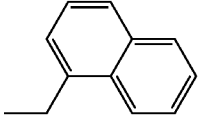 | N-{2-[2-(4-Amidinophenyl)-ethyl]-1-methyl-benzimidazol-5-yl}-N-( -naphthylmethyl)-[5-dimethylamino-pentanoic acid amide]-dihydrochloride |
| 26 | -Methyl | 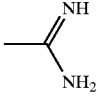 | 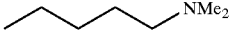 | 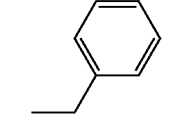 | N-{2-[2-(4-Amidinophenyl)-ethyl]-1-methyl-benzimidazol-5-yl}-N-benzyl-[5-dimethylamino-pentanoic acid amide]-dihydrochloride |
| 27 | -Methyl | 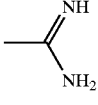 | 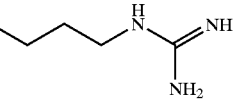 | 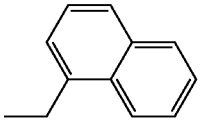 | N-{2-[2-(4-Amidinophenyl)-ethyl]-1-methyl-benzimidazol-5-yl}-N-(-naphthylmethyl)-[5-guanidino-pentanoic acid amide]-dihydrochloride |
| 28 | -Methyl | 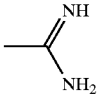 | 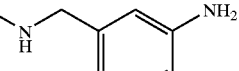 | 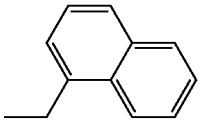 | N-{2-[2-(4-Amidinophenyl)-ethyl]-1-methyl-benzimidazol-5-yl}-N-( -naphthylmethy)-[3-aminobenzylamino-acetamide]-trihydrochloride |
| 29 | -Methyl | 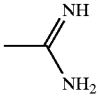 | 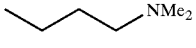 | 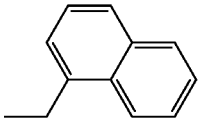 | N-{2-[2-(4-Amidinophenyl)-ethyl]-1-methyl-benzimidazol-5-yl}-N-( -naphthylmethyl)-[4-dimethylamino-butanoic acid amide]-dihydrochloride |
| 30 | -Methyl | 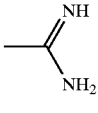 | 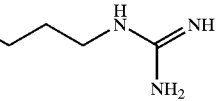 | 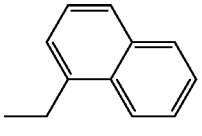 | N-{2-[2-(4-Amidinophenyl)-ethyl]-1-methyl-benzimidazol-5-yl}-N-( -naphthylmethyl)-[4-guanidino-butanoic acid amide]-dihydrochloride |

TABLE 1-continued

| No | -R¹ | -R² | -R³ | -R⁴ | Chemical name |
|---|---|---|---|---|---|
| 31 | -Methyl |  | 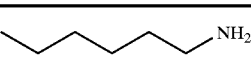 | 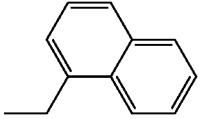 | N-{2-[2-(4-Amidinophenyl)-ethyl]-1-methyl-benzimidazol-5-yl}-N-(-naphthylmethyl)-[6-amino-hexanoic acid amide]-dihydrochloride |
| 32 | -Methyl |  | 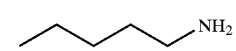 | 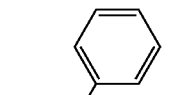 | N-{2-[2-(4-Amidinophenyl)-ethyl]-1-methyl-benzimidazol-5-yl}-N-benzyl-[5-amino-pentanoic acid amide]-dihydrochloride |
| 33 | -Methyl |  | 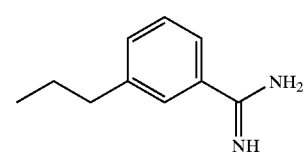 | 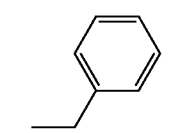 | N-{2-[2-(4-Amidinophenyl)-ethyl]-1-methyl-benzimidazol-5-yl}-N-benzyl-[3-(3-amidinophenyl)-propionamide]-dihydrochloride |
| 34 | -Methyl |  | 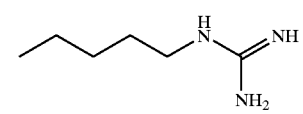 | 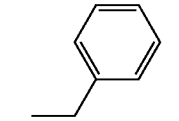 | N-{2-[2-(4-Amidinophenyl)-ethyl]-1-methyl-benzimidazol-5-yl}-N-benzyl-[5-guanidino-pentanoic acid amide]-dihydrochloride |
| 35 | -Methyl |  | 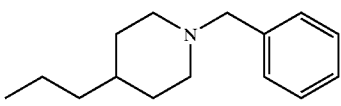 | 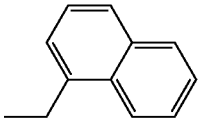 | N-{2-[2-(4-Amidinophenyl)-ethyl]-1-methyl-benzimidazol-5-yl}-N-(-naphthylmethyl)-[3-(1-benzyl-piperidin-4-yl)-propionamide]-dihydrochloride |
| 36 | -Methyl |  | 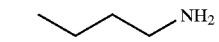 | 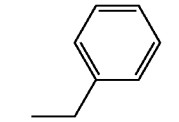 | N-{2-[2-(4-Amidinophenyl)-ethyl]-1-methyl-benzimidazol-5-yl}-N-benzyl-[4-amino-butanoic acid amide]-dihydrochloride |
| 37 | -Methyl |  | 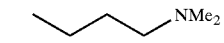 | 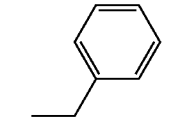 | N-{2-[2-(4-Amidinophenyl)-ethyl]-1-methyl-benzimidazol-5-yl}-N-benzyl-[4-dimethyl-amino-butanoic acid amide]-dihydrochloride |
| 38 | -Methyl |  | 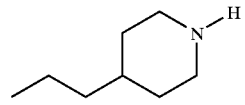 | 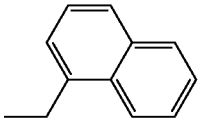 | N-{2-[2-(4-Amidinophenyl)-ethyl]-1-methyl-benzimidazol-5-yl}-N-(-naphthylmethyl)-[3-(piperidin-4-yl)-propionamide]-dihydrochloride |
| 39 | -Methyl |  | 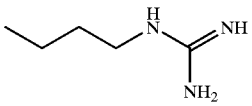 | 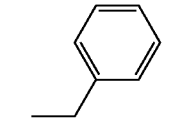 | N-{2-[2-(4-Amidinophenyl)-ethyl]-1-methyl-benzimidazol-5-yl}-N-benzyl-[4-guanidino-butanoic acid amide]-dihydrochloride |
| 40 | -Methyl |  | 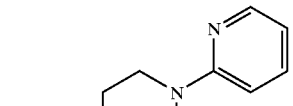 | 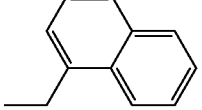 | N-{2-[2-(4-Amidinophenyl)-ethyl]-1-methyl-benzimidazol-5-yl}-N-(-naphthylmethyl)-[2-(1-pyridin-2-yl-piperazin-4-yl)-acetamide]-dihydrochloride |

TABLE 1-continued

| No | -R¹ | -R² | -R³ | -R⁴ | Chemical name |
|---|---|---|---|---|---|
| 41 | -Methyl |  | 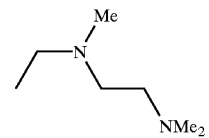 | 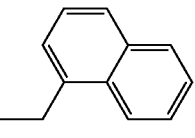 | N-{2-[2-(4-Amidinophenyl)-ethyl]-1-methyl-benzimidazol-5-yl}-N-(α-naphthylmethyl)-[2-(N-(2-dimethylaminoethyl)-N-methylamino)-acetamide]-trihydrochloride |
| 42 | -Methyl |  | 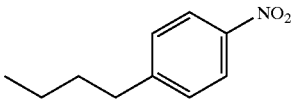 | 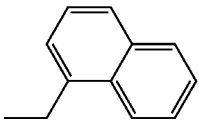 | N-{2-[2-(4-Amidinophenyl)-ethyl]-1-methyl-benzimidazol-5-yl}-N-(α-naphthylmethyl)-[4-(4-nitrophenyl)-butyroamide]-hydrochloride |
| 43 | -Methyl |  | 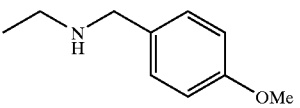 | 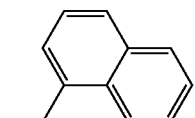 | N-{2-[2-(4-Amidinophenyl)-ethyl]-1-methyl-benzimidazol-5-yl}-N-(-naphthylmethyl)-[2-(4-methoxybenzylamino)-acetamide]-dihydrochloride |
| 44 | -Methyl |  | 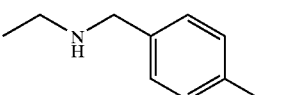 | 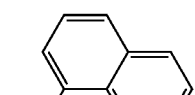 | N-{2-[2-(4-Amidinophenyl)-ethyl]-1-methyl-benzimidazol-5-yl}-N-( -naphthylmethylamino)-[2-(4-trifluoromethylbenzylamino)-acetamide]-dihydrochloride |
| 45 | -Methyl |  | 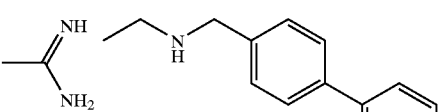 | 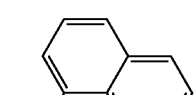 | N-{2-[2-(4-Amidinophenyl)-ethyl]-1-methyl-benzimidazol-5-yl}-N-( -naphthylmethyl)-[2-(4-phenylbenzylamino)-acetamide]-dihydrochloride |
| 46 | -Methyl |  | 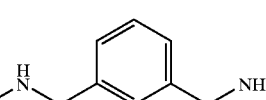 | 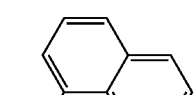 | N-{2-[2-(4-Amidinophenyl)-ethyl]-1-methyl-benzimidazol-5-yl}-N-( -naphthylmethyl)-[2-(3-amidinobenzylamino)-acetamide]-trihydrochloride |
| 47 | -Methyl |  | 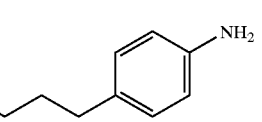 | 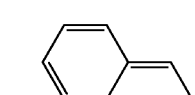 | N-{2-[2-(4-Amidinophenyl)-ethyl]-1-methyl-benzimidazol-5-yl}-N-( -naphthylmethyl)-[4-(4-aminophenyl)-butyroamide]-dihydrochloride |
| 48 | -Methyl |  | 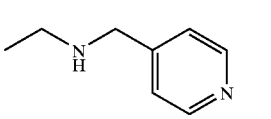 | 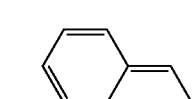 | N-{2-[2-(4-Amidinophenyl)-ethyl]-1-methyl-benzimidazol-5-yl}-N-( -naphthylmethyl)-[2-(pyridin-4-ylmethylamino)-acctamide]-dihydrochloride |
| 49 | -Methyl |  | 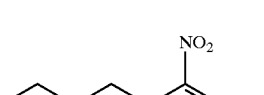 | 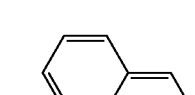 | N-{2-[2-(4-Amidinophenyl)-ethyl]-1-methyl-benzimidazol-5-yl}-N-( -naphthylmethyl)-[2-(2-nitrobenzylamino)-acctamide]-dihydrochloride |
| 50 | -Methyl |  | 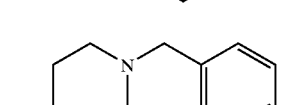 | 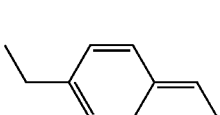 | N-{2-[2-(4-Amidinophenyl)-ethyl]-1-methyl-benzimidazol-5-yl}-N-β-naphthylmethyl)-[3-(1-benzylpiperidin-4-yl)-propionamide]-dihydrochloride |

TABLE 1-continued

| No | -R¹ | -R² | -R³ | -R⁴ | Chemical name |
|---|---|---|---|---|---|
| 51 | -Methyl | 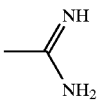 | 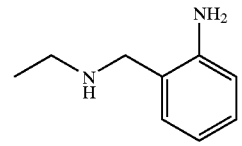 | 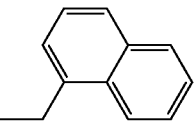 | N-{2-[2-(4-Amidinophenyl)-ethyl]-1-methyl-benzimidazol-5-yl}-N-( -naphthylmethyl)-[2-(2-aminobenzylamino)-acetamide]-trihydrochloride |
| 52 | -Methyl | 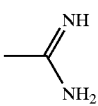 | 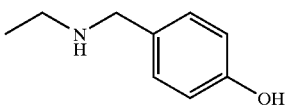 | 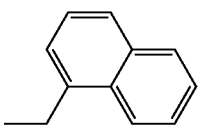 | N-{2-[2-(4-Amidinophenyl)-ethyl]-1-methyl-benzimidazol-5-yl}-N-( -naphthylmethyl)-[2-(4-hydroxybenzylamino)-acetamide]-dihydrochloride |
| 53 | -Methyl | 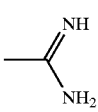 | 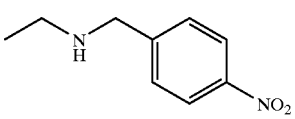 | 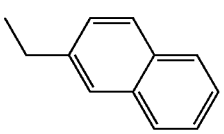 | N-{2-[2-(4-Amidinophenyl)-ethyl]-1-methyl-benzimidazol-5-yl}-N-(β-naphthylmethyl)-[2-(4-nitrobenzylamino)-acetamide]-hydrochloride |
| 54 | -Methyl | 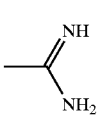 | 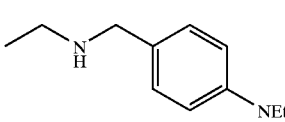 | 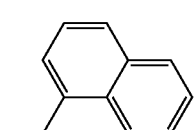 | N-{2-[2-(4-Amidinophenyl)-ethyl]-1-methyl-benzimidazol-5-yl}-N-( -naphthylmethyl)-[2-(4-diethylaminobenzylamino)-acetamide]-dihydrochloride |
| 55 | -Methyl | 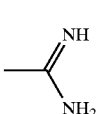 | 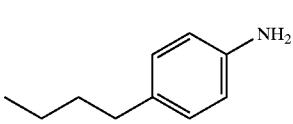 | 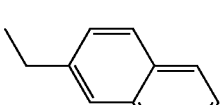 | N-{2-[2-(4-Amidinophenyl)-ethyl]-1-methyl-benzimidazol-5-yl}-N-(β-naphthylmethyl)-[4-(4-aminophenyl)-butyroamide]-dihydrochloride |
| 56 | -Methyl | 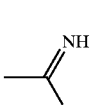 | 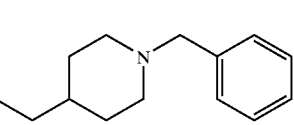 | 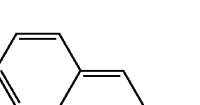 | N-{2-[2-(4-Amidinophenyl)-ethyl]-1-methyl-benzimidazol-5-yl}-N-(anthracen-9-ylmethyl)-[3-(1-benzyl-piperidin-4-yl)-propionamide]-dihydrochloride |
| 57 | -Methyl | 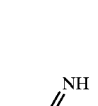 | 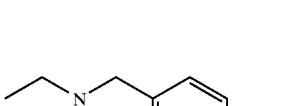 | 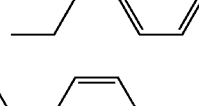 | N-{2-[2-(4-Amidinophenyl)-ethyl]-1-methyl-benzimidazol-5-yl}-N-(β-naphthylmethyl)-[4-methoxybenzylamino-acetamide]-dihydrochloride |
| 58 | -Methyl | 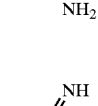 | 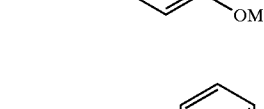 | 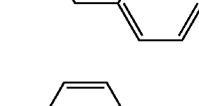 | N-{2-[2-(4-Amidinophenyl)-ethyl]-1-methyl-benzimidazol-5-yl}-N-( -naphthylmethyl)-[2-(1-(2-methoxyphenyl)-piperazin-4-yl)-acetamide]-dihydrochloride |
| 59 | -Methyl | 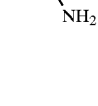 | 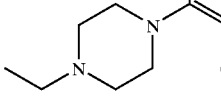 | 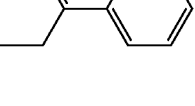 | N-{2-[2-(4-Amidinophenyl)-ethyl]-1-methyl-benzimidazol-5-yl}-N-(α-naphthylmethyl)-[2-(2-dimethylaminoethoxy)-acetamide]-dihydrochloride |
| 60 | -Methyl | 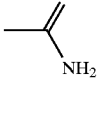 | 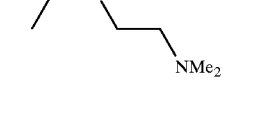 | 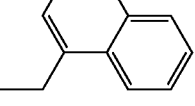 | N-{2-[2-(4-Amidinophenyl)-ethyl]-1-methyl-benzimidazol-5-yl}-N-(-naphthylmethyl)-[2-(4-methylbenzylamino)-acetamide]-dihydrochloride |

TABLE 1-continued

| No | -R¹ | -R² | -R³ | -R⁴ | Chemical name |
|---|---|---|---|---|---|
| 61 | -Methyl |  | 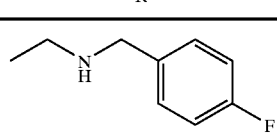 | 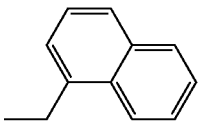 | N-{2-[2-(4-Amidinophenyl)-ethyl]-1-methyl-benzimidazol-5-yl}-N-( -naphthylmethyl)-[2-(4-fluorobenzylamino)-acetamide]-dihydrochloride |
| 62 | -Methyl |  | 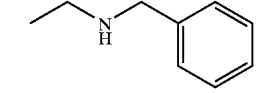 | 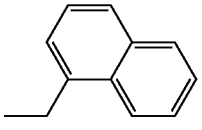 | N-{2-[2-(4-Amidinophenyl)-ethyl]-1-methyl-benzimidazol-5-yl}-N-( -naphthylmethyl)-[2-(N-benzylamino)-acetamide]-dihydrochloride |
| 63 | -Methyl |  | 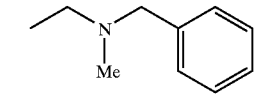 | 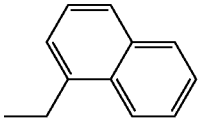 | N-{2-[2-(4-Amidinophenyl)-ethyl]-1-methyl-benzimidazol-5-yl}-N-( -naphthylmethyl)-[2-(N-benzyl-N-methylamino)-acetamide]-dihydrochloride |
| 64 | -Methyl |  | 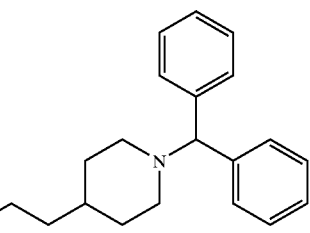 | 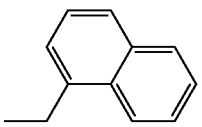 | N-{2-[2-(4-Amidinophenyl)-ethyl]-1-methyl-benzimidazol-5-yl}-N-( -naphthylmethyl)-[3-(1-diphenylmethyl-piperidin-4-yl)-propionamide]-trihydrochloride |
| 65 | -Methyl |  | 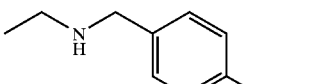 | 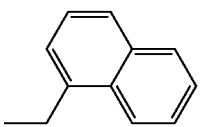 | N-{2-[2-(4-Amidinophenyl)-ethyl]-1-methyl-benzimidazol-5-yl}-N-( -naphthylmethyl)-[2-(4-ethylcarboxylatbenzylamino)-acetamide]-dihydrochloride |
| 66 | -Methyl |  |  | 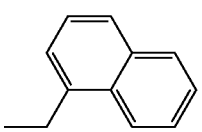 | N-{2-[2-(4-Amidinophenyl)-ethyl]-1-methyl-benzimidazol-5-yl}-N-( -naphthylmethyl)-[2-diethylamino acetamide]-dihydrochloride |
| 67 | -Methyl |  | 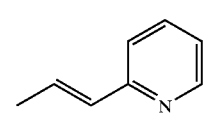 | 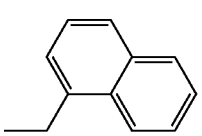 | N-{2-[2-(4-Amidinophenyl)-ethyl]-1-methyl-benzimidazol-5-yl}-N-( -naphthylmethyl)-[3-(pyridin-2-yl)-acrylamide]-hydrochloride |
| 68 | -Methyl |  | 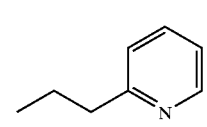 | 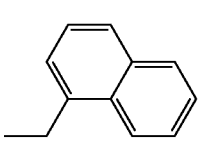 | N-{2-[2-(4-Amidinophenyl)-ethyl]-1-methyl-benzimidazol-5-yl}-N-( -naphthylmethyl)-[3-(pyridin-2-yl)-propionamide]-hydrochloride |
| 69 | -Methyl |  | 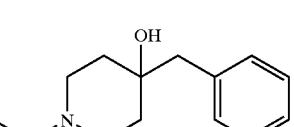 | 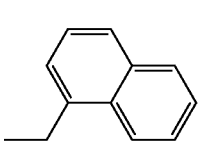 | N-{2-[2-(4-Amidinophenyl)-ethyl]-1-methyl-benzimidazol-5-yl}-N-( -naphthylmethyl)-[2-(4-benzyl-4-hydroxypiperidin-1-yl)-acetamide]-dihydrochloride |
| 70 | -Methyl |  | 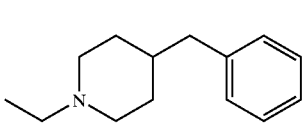 | 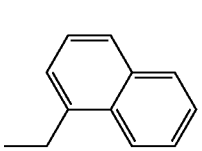 | N-{2-[2-(4-Amidinophenyl)-ethyl]-1-methyl-benzimidazol-5-yl}-N-( -naphthylmethyl)-[2-(4-benzyl-4-piperidin-1-yl)-acetamide]-dihydrochloride |

TABLE 1-continued

| No | -R¹ | -R² | -R³ | -R⁴ | Chemical name |
|---|---|---|---|---|---|
| 71 | -Methyl | amidine (NH, NH₂) | 1-ethyl-piperidin-4-yl-COOEt | naphthylmethyl | N-{2-[2-(4-Amidinophenyl)-ethyl]-1-methyl-benzimidazol-5-yl}-N-( -naphthylmethyl)-[2-(4-ethylcarboxylate-4-piperidin-1-yl)-acetamide]-dihydrochloride |
| 72 | -Methyl | amidine (NH, NH₂) | 1-ethyl-pyrrolidin-2-S-CONH₂ | naphthylmethyl | N-{2-[2-(4-Amidinophenyl)-ethyl]-1-methyl-benzimidazol-5-yl}-N-( -naphthylmethyl)-[2-(2-S-carboxylic acid amide)-pyrrolidin-1-yl)-acetamide]-dihydrochloride |
| 73 | -Methyl | amidine (NH, NH₂) | ethyl-NH-CH₂-(4-aminophenyl) | 4-aminobenzyl | N-{2-[2-(4-Amidinophenyl)-ethyl]-1-methyl-benzimidazol-5-yl}-N-(4-aminobenzyl)-[2-(4-aminobenzylamino)-acetamide]-dihydrochloride |
| 74 | -Methyl | amidine (NH, NH₂) | ethyl-NH-CH₂-(4-aminophenyl) | pyridin-4-ylmethyl | N-{2-[2-(4-Amidinophenyl)-ethyl]-1-methyl-benzimidazol-5-yl}-N-(-pyridin-4-ylmethyl)-[2-(4-aminobenzylamino)-acetamide]-dihydrochloride |
| 75 | -Methyl | amidine (NH, NH₂) | ethyl-O-CH₂-(4-nitrophenyl) | naphthylmethyl | N-{2-[2-(4-Amidinophenyl)-ethyl]-1-methyl-benzimidazol-5-yl}-N-(--naphthylmethyl)-[2-(4-nitrobenzyloxy)-acetamide]-hydrochloride |
| 76 | -Methyl | amidine (NH, NH₂) | ethyl-NH-CH₂CH₂-NMe₂ | α-naphthylmethyl | N-{2-[2-(4-Amidinophenyl)-ethyl]-1-methyl-benzimidazol-5-yl}-N-(α-naphthylmethyl)-[2-N-(2-dimethylaminoethyl)-amino)-acetamide]-trihydrochloride |
| 77 | -Methyl | amidine (NH, NH₂) | ethyl-OH | naphthylmethyl | N-{2-[2-(4-Amidinophenyl)-ethyl]-1-methyl-benzimidazol-5-yl}-N-(-naphthylmethyl)-[3-hydroxy-acetamide]-hydrochloride |
| 78 | -Methyl | amidine (NH, NH₂) | ethyl-NH-CH₂CH₂CH₂-NMe₂ | α-naphthylmethyl | N-{2-[2-(4-Amidinophenyl)-ethyl]-1-methyl-benzimidazol-5-yl}-N-(α-naphthylmethyl)-[2-(N-(3-dimethylaminopropyl)-amino)-acetamide]-trihydrochloride |
| 79 | -Methyl | amidine (NH, NH₂) | 1-ethyl-4-(pyridin-2-ylmethyl)-piperazine | naphthylmethyl | N-{2-[2-(4-Amidinophenyl)-ethyl]-1-methyl-benzimidazol-5-yl}-N-( -naphthylmethyl)-[2-(1-pyridin-2-yl-piperazin-4-yl)-acetamide]-trihydrochloride |
| 80 | -Methyl | amidine (NH, NH₂) | ethyl-naphthyl | naphthylmethyl | N-{2-[2-(4-Amidinophenyl)-ethyl]-1-methyl-benzimidazol-5-yl}-N-( -naphthylmethyl)-[2-( -naphthyl)-acetamide]-hydrochloride |
| 81 | -Methyl | amidine (NH, NH₂) | ethyl-piperidin-1-yl | naphthylmethyl | N-{2-[2-(4-Amidinophenyl)-ethyl]-1-methyl-benzimidazol-5-yl}-N-( -naphthylmethyl)-[2-(piperidin-1-yl)-acetamide]-dihydrochloride |

TABLE 1-continued

| No | -R¹ | -R² | -R³ | -R⁴ | Chemical name |
|----|-----|-----|-----|-----|---------------|
| 82 | -Methyl | 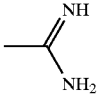 | 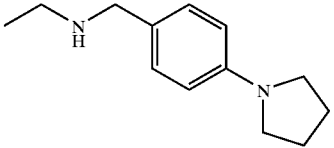 |  | N-{2-[2-(4-Amidinophenyl)-ethyl]-1-methyl-benzimidazol-5-yl}-N-( -naphthylmethyl)-[2-(N-4-pyrrolidin-1-ylbenzylamino)-acetamide]-dihydrochloride |
| 83 | -Methyl | 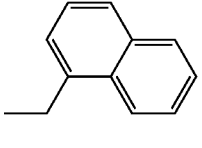 | 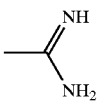 | 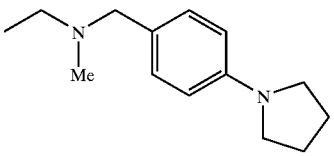 | N-{2-[2-(4-Amidinophenyl)-ethyl]-1-methyl-benzimidazol-5-yl}-N-( -naphthylmethyl)-[2-(N-(4-pyrrolidin-1-ylbenzyl)-N-methylamino)-acetamide]-dihydrochloride |

The compounds according to the invention are characterised by their tryptase-inhibiting activity. This ability to inhibit tryptase was investigated using the test described as follows. The measurement is carried out in Tris HCl buffer (100 mM), which additionally contains calcium (5 mM) and heparin (100 mg/ml), at pH 7.4. The standard used is rh beta tryptase which may be obtained commercially from Promega, for example. The substrate used is N-p-tosyl-Gly-Pro-Lys-para-nitroaniline in a concentration of 0.6 mM. The substrate is digested with tryptase to form p-nitroaniline which can be measured at 405 nm. Usually, an incubation period of 5 minutes and an incubation temperature of 37° C. are chosen. The enzyme activity used is 0.91 U/ml. The measurements are carried out in an Autoanalyser (Cobas Bio) made by Hofmann LaRoche. The potential inhibitory substances are used in concentrations of 10 $\mu$M in the screening, the inhibition of the tryptase being given in percent. The $IC_{50}$ is determined at over 70% inhibition (concentration at which 50% of the enzyme activity is inhibited). After 5 minutes' pre-incubation of the potential inhibitory substances, the substrate is added to start the reaction, the formation of p-nitroaniline being taken as a measurement of the enzyme activity after 5 minutes, after testing the linearity.

The data obtained after the above test has been carried out (IC50 values) can be found in Table 2:

TABLE 2

| Example | $IC_{50}$ [$\mu$M] |
|---------|---------------------|
| 1 | 0.064 |
| 2 | 0.19 |
| 3 | 0.049 |
| 4 | 0.055 |
| 5 | 0.061 |
| 7 | 0.108 |
| 8 | 0.016 |
| 9 | 0.024 |
| 10 | 0.016 |
| 11 | 0.015 |
| 12 | 0.03 |
| 18 | 0.012 |
| 19 | 0.016 |
| 20 | 0.039 |
| 21 | 0.011 |
| 22 | 0.01 |
| 23 | 0.007 |
| 24 | 0.029 |

TABLE 2-continued

| Example | $IC_{50}$ [$\mu$M] |
|---------|---------------------|
| 25 | 0.033 |
| 26 | 0.053 |
| 27 | 0.026 |
| 28 | 0.01 |
| 29 | 0.038 |
| 30 | 0.032 |
| 31 | 0.03 |
| 32 | 0.057 |
| 33 | 0.026 |
| 34 | 0.043 |
| 35 | 0.014 |
| 36 | 0.07 |
| 37 | 0.076 |
| 38 | 0.047 |
| 39 | 0.077 |
| 40 | 0.013 |
| 41 | 0.018 |
| 42 | 0.011 |
| 43 | 0.01 |
| 44 | 0.031 |
| 45 | 0.012 |
| 46 | 0.027 |
| 47 | 0.012 |
| 48 | 0.038 |
| 49 | 0.013 |
| 50 | 0.072 |
| 51 | 0.025 |
| 52 | 0.012 |
| 53 | 0.092 |
| 54 | 0.0086 |
| 55 | 0.172 |
| 56 | 0.0906 |
| 57 | 0.026 |
| 58 | 0.019 |
| 59 | 0.066 |
| 60 | 0.025 |
| 61 | 0.039 |
| 62 | 0.029 |
| 63 | 0.028 |
| 64 | 0.025 |
| 65 | 0.027 |
| 66 | 0.027 |
| 67 | 0.039 |
| 68 | 0.038 |
| 69 | 0.018 |
| 70 | 0.0039 |
| 71 | 0.0159 |
| 72 | 0.0584 |
| 73 | 0.0131 |
| 74 | 0.0574 |
| 75 | 0.0172 |

TABLE 2-continued

| Example | IC$_{50}$ [μM] |
|---|---|
| 76 | 0.022 |
| 77 | 0.1096 |
| 78 | 0.0213 |
| 79 | 0.0201 |
| 80 | 0.0301 |
| 81 | 0.0631 |
| 82 | 0.0049 |
| 83 | 0.0076 |

The tryptase inhibitors according to the invention may be administered orally, transdermally, by inhalation or parenterally. The compounds according to the invention occur as active ingredients in conventional preparations, for example in compositions which consist essentially of an inert pharmaceutical carrier and an effective dose of the active substance, such as for example tablets, coated tablets, capsules, powders, solutions, suspensions, emulsions, syrups, suppositories, transdermal systems etc. An effective dose of the compounds according to the invention is between 1 and 100, preferably between 1 and 50, most preferably between 5–30 mg/dose for oral administration, and between 0.001 and 50, preferably between 0.1 and 10 mg/dose for intravenous or intramuscular administration. For inhalation, according to the invention, solutions containing 0.01 to 1.0, preferably 0.1 to 0.5% active substance are suitable. For administration by inhalation the use of powders is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable preparations include for example tablrts, capsules, suppositories, solutions, elixirs, emulsions or dispersible powders. Suitable tables may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 800 mg, preferably 10–300 mg per adult.

The Examples which follow illustrate the present invention without restricting its scope:

Examples of Pharmaceutical Formulations

| A) | Tablets | per tablet |
|---|---|---|
| | active substance | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | Active substance | 5 mg |
| | Corn starch | 41.5 mg |
| | Lactose | 30 mg |

-continued

| C) | Coated tablets | per coated tablet |
|---|---|---|
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Active substance | 50 mg |
| | Corn starch | 268.5 mg |
| | Magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloridee | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The hard fat is melted. At 40° C. the ground active substance is homogeneously dispersed. It is cooled to 38° C. and poured into slightly chilled suppository moulds.

What is claimed is:
1. A compound of the formula (I)

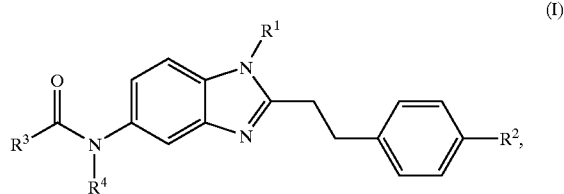

wherein:
R$^1$ denotes a group selected from the group consisting of C$_1$–C$_6$-alkyl, C$_2$–C$_6$-alkenyl and C$_2$–C$_6$-alkynyl, which is optionally mono-, di- or trisubstituted by one or more of the groups hydroxy, C$_1$–C$_4$-alkoxy, CF$_3$, phenoxy, COOH, halogen, —CO(C$_1$–C$_4$-alkoxy), —CO—NR$^5$R$^6$, —NR$^5$R$^6$ or C$_1$–C$_4$-alkoxy-phenoxy, or phenyl-C$_1$–C$_4$-alkyl, which is optionally mono-, di- or trisubstituted by one or more of the groups hydroxy, C$_1$–C$_4$-alkoxy, carboxy, halogen, C$_1$–C$_4$-alkoxycarbonyl or CF$_3$, or a 5- or 6-membered, saturated or unsaturated heterocycle linked directly or via a C$_1$–C$_4$-alkylene bridge, which may contain one or two heteroatoms selected from the group consisting of oxygen, nitrogen and sulphur and which may optionally be substituted by C$_1$–C$_4$-alkyl or benzyl;

R$^2$ denotes —C(=NH)NH$_2$ or —CH$_2$—NH$_2$;

R$^3$ denotes a C$_1$–C$_6$-alkyl, C$_1$–C$_6$-hydroxyalkyl or C$_1$–C$_4$-alkoxy-C$_1$–C$_4$-alkyl group which may be mono- or disubstituted by one, two or three of the groups —NR$^5$R$^6$, —C(=NH)NH$_2$ or —NH—C(=NH)NH$_2$, or a 5-, 6- or 7-membered, saturated or unsaturated heterocycle linked directly or via a C$_1$–C$_4$-alkylene bridge or a C$_2$–C$_4$-alkenylene bridge, which may contain one, two or three heteroatoms selected from the group consisting of oxygen, nitrogen and sulphur and which is optionally mono- or disubstituted by hydroxy, C$_1$–C$_4$-alkyl, —COO—C$_1$–C$_4$-alkyl, —CONH$_2$, benzyl, diphenylmethyl, phenyl or pyridylmethyl, pyridyl, and wherein the phenyl substituent may be mono-, di- or trisubstituted by one or more groups selected from the group consisting of C$_1$–C$_4$-alkyl, C$_1$–C$_4$-alkoxy, halogen, C$_1$–C$_4$-alkyl-halogen and —NH$_2$, cyclopropyl, cyclobutyl, cyclopentyl or cyclohexyl, each of which may be mono- or disubstituted by one or two of the groups —NR$^5$R$^6$, —C(=NH)NH$_2$ or —NH—C(=NH)NH$_2$, or phenyl-C$_1$–C$_4$-alkyl or naphthyl-C$_1$–C$_4$-alkyl, which is optionally substituted at the alkylene bridge by —NR$^5$R$^6$ and may be mono- or disubstituted at the phenyl ring by one or two of the groups —NO$_2$, —NR$^5$R$^6$, —C$_1$–C$_4$-alkyl-NR$^5$R$^6$, —C(=NH)NH$_2$ or —NH—C(=NH)NH$_2$;

R$^4$ denotes C$_1$–C$_6$-alkyl, which is mono- or disubstituted by one or two groups selected from the group consisting of furanyl, benzofuranyl, thiophenyl, benzothiophenyl, anthracenyl, phenyl, pyridyl and naphthyl, while the substituents phenyl and naphthyl may in turn be mono-, di- or trisubstituted by one or more of the groups selected from the group consisting of C$_1$–C$_4$-alkyl, C$_1$–C$_4$-alkoxy, halogen, C$_1$–C$_4$-alkylhalogen, —NH$_2$, —NH(C$_1$–C$_4$-alkyl), —N(C$_1$–C$_4$-alkyl)$_2$, NO$_2$, hydroxy, —CF$_3$, —NHCO—C$_1$–C$_4$-alkyl, —COOH, —COO(C$_1$–C$_4$-alkyl), —CONH$_2$, —CONH(C$_1$–C$_4$-alkyl), —CON(C$_1$–C$_4$-alkyl)$_2$, —CONH(C$_1$–C$_4$-alkyl)-COO(C$_1$–C$_4$-alkyl) and phenyl-C$_1$–C$_6$-alkyl; and, R$^5$ and R$^6$, which may be identical or different, denote hydrogen, C$_1$–C$_4$-alkyl, phenyl, pyridyl or benzyl, which is optionally substituted by a group selected from the group consisting of halogen, halo-C$_1$–C$_4$-alkyl, —OH, C$_1$–C$_4$-alkyl, —O—C$_1$–C$_4$-alkyl, —CO—O—C$_1$–C$_4$-alkyl, —NO$_2$, phenyl, pyrrolidin-1-yl, piperidin-1-yl, —NH$_2$, —NH—C$_1$–C$_4$-alkyl, —N(C$_1$–C$_4$-alkyl)$_2$ and —C(=NH)NH$_2$—NH$_2$, or a tautomer or pharmaceutically acceptable salt thereof.

2. A compound of the formula (I) according to claim 1 wherein:

R$^1$ denotes C$_1$–C$_6$-alkyl, which is optionally mono-, di- or trisubstituted by one or more of the groups hydroxy, C$_1$–C$_4$-alkoxy, CF$_3$, phenoxy, COOH, halogen, —CO(C$_1$–C$_4$-alkoxy), —CO—NR$^5$R$^6$, —NR$^5$R$^6$ or C$_1$–C$_4$-alkoxy-phenoxy, or R$^2$ denotes —C(=NH)NH$_2$ or —CH$_2$—NH$_2$;

R$^3$ denotes a C$_1$–C$_6$-alkyl group, which may be mono- or disubstituted by one or two of the groups —NR$^5$R$^6$, —C(=NH)NH$_2$ or —NH—C(=NH)NH$_2$, or a 5-, 6- or 7-membered, saturated or unsaturated heterocycle linked directly or via a C$_1$–C$_4$-alkylene bridge, which may contain one, two or three heteroatoms selected from the group consisting of oxygen, nitrogen and sulphur and is optionally mono- or disubstituted by hydroxy, C$_1$–C$_4$-alkyl, benzyl, phenyl or pyridyl, and wherein the phenyl substituent may be substituted by one of the groups selected from the group consisting of C$_1$–C$_3$-alkyl, C$_1$–C$_3$-alkoxy, halogen, trifluoromethyl and NH$_2$, cyclopropyl, cyclopentyl or cyclohexyl, each of which may be mono- or disubstituted by one or two of the groups —NR$^5$R$^6$, —C(=NH)NH$_2$ or —NH—C(=NH)NH$_2$, or phenyl-C$_1$–C$_4$-alkyl or naphthyl-C$_1$–C$_4$-alkyl, which is optionally substituted by —NR$^5$R$^6$ at the alkylene bridge and may be mono- or disubstituted at the phenyl ring by one or two of the groups —NO$_2$, —NR$^5$R$^6$, —C$_1$–C$_4$-Alkyl-NR$^5$R$^6$, —C(=NH)NH$_2$ or —NH—C(=NH)NH$_2$, R$^4$ denotes C$_1$–C$_6$-alkyl, which is mono- or disubstituted by one or two groups selected from the group consisting of phenyl, pyridyl and naphthyl, wherein the substituents phenyl and naphthyl may in turn be substituted by one of the groups selected from the group consisting of C$_1$–C$_4$-alkyl, C$_1$–C$_4$-alkoxy, halogen, —C$_1$–C$_4$-alkyl-halogen and —NH$_2$; and R$^5$ and R$^6$, which may be identical or different, denote hydrogen, C$_1$–C$_4$-alkyl, pyridyl or benzyl, which is optionally substituted by a group selected from the group consisting of —OH, —O—C$_1$–C$_3$-alkyl, —NO$_2$, phenyl, pyrrolidin-1-yl, —NH$_2$, —NH—C$_1$–C$_4$-alkyl, —N(C$_1$–C$_4$-alkyl)$_2$ and —C(=NH)NH$_2$, or a tautomer or pharmaceutically acceptable salt thereof.

3. A compound of the formula (I) according to claim 1, wherein:

R$^1$ denotes C$_1$–C$_4$-alkyl, which is optionally mono-, di- or trisubstituted by one or more of the groups hydroxy, C$_1$–C$_4$-alkoxy, CF$_3$, phenoxy, COOH, halogen, —CO(C$_1$–C$_4$-alkoxy), —CO—NR$^5$R$^6$, —NR$^5$R$^6$ or C$_1$–C$_4$-alkoxy-phenoxy, or R$^2$ denotes —C(=NH)NH$_2$ or —CH$_2$—NH$_2$;

R$^3$ denotes a C$_1$–C$_4$-alkyl group, which may be mono- or disubstituted by one or two of the groups —NR$^5$R$^6$, —C(=NH)NH$_2$ or —NH—C(=NH)NH$_2$, or a 5-, 6- or 7-membered, saturated or unsaturated heterocycle linked directly or via a methylene or ethylene bridge, which may contain one or two heteroatoms selected from the group consisting of oxygen and nitrogen and is optionally substituted by methyl or benzyl;

naphthylmethyl, benzyl or phenylethyl, which is optionally substituted by —NR$^5$R$^6$ at the alkylene bridge and may be substituted at the phenyl ring by a group selected from the group consisting of —NR$^5$R$^6$, —C$_1$–C$_4$-alkyl-NR$^5$R$^6$, —C(=NH)NH$_2$ and —NH—C(=NH)NH$_2$, R$^4$ denotes C$_1$–C$_5$-alkyl, which is mono- or disubstituted by one or two groups selected from the group consisting of phenyl, pyridyl and naphthyl; and, R$^5$ and R$^6$, which may be identical or different, denote hydrogen, methyl, ethyl, propyl, butyl, pyridyl or benzyl, which is optionally substituted by a group selected from the group consisting of —OH, methoxy, —NO$_2$, phenyl, pyrrolidin-1-yl, —NH$_2$, —NH-methyl, —N(methyl)$_2$, —NH-ethyl, —N(ethyl)$_2$ and —C(=NH)NH$_2$, or a tautomer or pharmaceutically acceptable salt thereof.

4. A compound of the formula (I) according to claim 1, wherein:

R$^1$ denotes methyl, ethyl, propyl or butyl;

R$^2$ denotes —C(=NH)NH$_2$ or —CH$_2$—NH$_2$;

R$^3$ denotes a C$_2$–C$_4$-alkyl group, which may be mono- or disubstituted by one or two of the groups —NR$^5$R$^6$, —C(=NH)NH$_2$ or —NH—C(=NH)NH$_2$, or a 6-membered, saturated or unsaturated heterocycle linked via a methylene or ethylene bridge, which contains one or two nitrogen atoms and is optionally substituted by methyl or benzyl;

naphthylmethyl, benzyl or phenylethyl, which is optionally substituted by —NR$^5$R$^6$ at the alkylene bridge and which are substituted at the phenyl ring by a group selected from the group consisting of —NR$^5$R$^6$, —C$_1$–C$_4$-alkyl-NR$^5$R$^6$, —C(=NH)NH$_2$ and —NH—C(=NH)NH$_2$, R$^4$ denotes an alkyl group selected from the group consisting of methyl, ethyl, propyl, butyl and pentyl, which is mono- or disubstituted by one or two groups selected from the group consisting of phenyl, pyridyl and naphthyl; and, R$^5$ and R$^6$, which may be identical or different, denote hydrogen, methyl, ethyl, propyl, butyl, pyridyl or benzyl, which is optionally substituted by a group selected from the group consisting of —OH, methoxy, —NO$_2$, phenyl, pyrrolidin-1-yl, —NH$_2$, —NH-methyl, —N(methyl)$_2$ and —C(=NH) NH$_2$, or a tautomer or pharmaceutically acceptable salt thereof.

5. A compound of the formula (I) according to claim 1, wherein:

R$^1$ denotes methyl, ethyl or propyl;

R$^2$ denotes —C(=NH)NH$_2$ or —CH$_2$—NH$_2$;

R$^3$ denotes methyl which is substituted by a group selected from the group consisting of pyridylamino, benzylamino, N-benzyl-N-methylamino, N-(amidinobenzyl)amino, N-(amidinobenzyl)-N- methyl-amino, N-(dimethylaminobenzyl)amino, (pyrrolidin-1-ylbenzyl)amino and N-(dimethylaminobenzyl)-N-methyl-amino, or an alkyl group selected from the group consisting of ethyl and propyl, which may be mono- or disubstituted by one or two groups selected from the group consisting of —NH$_2$ and —NH—C(=NH)NH$_2$, or a heterocycle linked via an ethylene bridge, selected from the group consisting of piperidine, morpholine and piperazine, which is optionally substituted by methyl, benzyl or diphenylmethyl;

phenylethyl, which is optionally substituted by —NH$_2$ at the ethylene bridge and is substituted at the phenyl ring by a group selected from the group consisting of pyrrolidin-1-yl, —NH$_2$, —N(methyl)$_2$, —CH$_2$—NH$_2$ and —C(=NH)NH$_2$; and, R$^4$ denotes benzyl, pyridylmethyl, naphthalinylmethyl or diphenylpropyl, or a tautomer or pharmaceutically acceptable salt thereof.

6. A compound of the formula (I) according to claim 1, wherein:

R$^1$ denotes methyl, ethyl or propyl;

R$^2$ denotes —C(=NH)NH$_2$ or —CH$_2$—NH$_2$;

R$^3$ denotes methyl, which is substituted by a group selected from the group consisting of N-(amidinobenzyl)amino, N-(amidinobenzyl)-N-methyl-amino, N-(dimethylaminobenzyl)amino, (pyrrolidin-1-ylbenzyl)amino and N-(dimethylaminobenzyl)-N-methyl-amino, or a piperidine or piperazine linked via an ethylene bridge, which is optionally substituted by benzyl;

phenylethyl, which is optionally substituted by —NH$_2$ at the ethylene bridge and is substituted by —C(=NH)NH$_2$ at the phenyl ring; and, R$^4$ denotes benzyl, naphthalinylmethyl or diphenylpropyl, or a tautomer or pharmaceutically acceptable salt thereof.

7. A compound of the formula (IA)

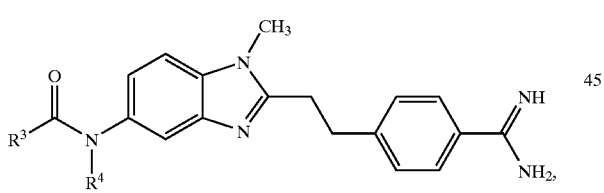

(IA)

wherein:

R$^3$ denotes methyl which is substituted by a group selected from the group consisting of N-(amidinobenzyl)amino, N-(amidinobenzyl)-N-methyl-amino, N-(dimethylaminobenzyl)amino, (pyrrolidin-1-ylbenzyl)amino, and N-(dimethylaminobenzyl)-N-methyl-amino, or a piperidine or piperazine linked via an ethylene bridge, which is optionally substituted by benzyl;

phenylethyl which is optionally substituted by —NH$_2$ at the ethylene bridge and which is substituted at the phenyl ring by —C(=NH)NH$_2$; and, R$^4$ denotes benzyl, naphthalinylmethyl or diphenylpropyl, or a tautomer of pharmaceutically acceptable salt thereof.

8. A compound of the formula (II)

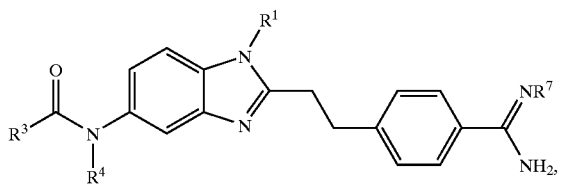

(II)

wherein:

R$^1$ denotes a group selected from the group consisting of C$_1$–C$_6$-alkyl, C$_2$–C$_6$-alkenyl and C$_2$–C$_6$-alkynyl, which is optionally mono-, di- or trisubstituted by one or more of the groups hydroxy, C$_1$–C$_4$-alkoxy, CF$_3$, phenoxy, COOH, halogen, —CO(C$_1$–C$_4$-alkoxy), —CO—NR$^5$R$^6$, —NR$^5$R$^6$ or C$_1$–C$_4$-alkoxy-phenoxy, or phenyl-C$_1$–C$_4$-alkyl, which is optionally mono-, di- or trisubstituted by one or more of the groups hydroxy, C$_1$–C$_4$-alkoxy, carboxy, halogen, C$_1$–C$_4$-alkoxycarbonyl or CF$_3$, or a 5- or 6-membered, saturated or unsaturated heterocycle linked directly or via a C$_1$–C$_4$-alkylene bridge, which may contain one or two heteroatoms selected from the group consisting of oxygen, nitrogen and sulphur and which is optionally substituted by C$_1$–C$_4$-alkyl or benzyl;

R$^3$ denotes a C$_1$–C$_6$-alkyl, C$_1$–C$_6$-hydroxyalkyl or C$_1$–C$_4$-alkoxy-C$_1$–C$_4$-alkyl group which may be mono- or disubstituted by one, two or three of the groups —NR$^5$R$^6$, —C(=NH)NH$_2$ or —NH—C(=NH)NH$_2$, or a 5-, 6- or 7-membered, saturated or unsaturated heterocycle linked directly or via a C$_1$–C$_4$-alkylene bridge or a C$_2$–C$_4$-alkenylene bridge, which may contain one, two or three heteroatoms selected from the group consisting of oxygen, nitrogen and sulphur and which is optionally mono- or disubstituted by hydroxy, C$_1$–C$_4$-alkyl, —COO—C$_1$–C$_4$-alkyl, —CONH$_2$, benzyl, diphenylmethyl, phenyl or pyridylmethyl, pyridyl, and wherein the phenyl substituent may be mono-, di- or trisubstituted by one or more groups selected from the group consisting of C$_1$–C$_4$-alkyl, C$_1$–C$_4$-alkoxy, halogen, C$_1$–C$_4$-alkyl-halogen and —NH$_2$, cyclopropyl, cyclobutyl, cyclopentyl or cyclohexyl, each of which may be mono- or disubstituted by one or two of the groups —NR$^5$R$^6$, —C(=NH)NH$_2$ or —NH—C(=NH)NH$_2$, or phenyl-C$_1$–C$_4$-alkyl or naphthyl-C$_1$–C$_4$-alkyl, which is optionally substituted at the alkylene bridge by —NR$^5$R$^6$ and may be mono- or disubstituted at the phenyl ring by one or two of the groups —NO$_2$, —NR$^5$R$^6$, —C$_1$–C$_4$-alkyl-NR$^5$R$^6$, —C(=NH)NH$_2$ or —NH—C(=NH)NH$_2$, or C$_1$–C$_4$-alkyl, which is substituted by a group selected from the group consisting of —C(=NOH)NH$_2$, —C(=NCOO—C$_1$–C$_{12}$-alkyl)NH$_2$ and —C(=NCOO—C$_1$–C$_8$-alkyl-phenyl)NH$_2$;

R$^4$ denotes C$_1$–C$_6$-alkyl, which is mono- or disubstituted by one or two groups selected from the group consisting of furanyl, benzofuranyl, thiophenyl, benzothiophenyl, anthracenyl, phenyl, pyridyl and naphthyl, while the substituents phenyl and naphthyl may in turn be mono-, di- or trisubstituted by one or more of the groups selected from the group consisting of $C_1$–$C_4$-alkyl, $C_1$–$C_4$-alkoxy, halogen, $C_1$–$C_4$-alkyl-halogen, —$NH_2$, —$NH(C_1$–$C_4$-alkyl), —$N(C_1$–$C_4$-alkyl)$_2$, $NO_2$, hydroxy, —$CF_3$, —NHCO—$C_1$–$C_4$-alkyl, —COOH, —COO($C_1$–$C_4$-alkyl), —$CONH_2$, —CONH($C_1$–$C_4$-alkyl), —CON($C_1$–$C_4$-alkyl)$_2$, —CONH($C_1$–$C_4$-alkyl)—COO($C_1$–$C_4$-alkyl) and phenyl-$C_1$–$C_6$-alkyl;

$R^5$ and $R^6$, which may be identical or different, denote hydrogen, $C_1$–$C_4$-alkyl, phenyl, pyridyl or benzyl, which is optionally substituted by a group selected from the group consisting of halogen, halo-$C_1$–$C_4$-alkyl, —OH, $C_1$–$C_4$-alkyl, —O—$C_1$–$C_4$-alkyl, —CO—O—$C_1$–$C_4$-alkyl, —$NO_2$, phenyl, pyrrolidin-1-yl, piperidin-1-yl, —$NH_2$, —NH—$C_1$–$C_4$-alkyl, —N($C_1$–$C_4$-alkyl)$_2$ and —C(=NH)$NH_2$—$NH_2$; and, $R^7$ denotes hydroxy, —COO—$C_1$–$C_{12}$-alkyl, —CO-phenyl, —CO-pyridyl or —COO—$C_1$–$C_8$-alkyl-phenyl, whilst in the abovementioned group the phenyl ring may be substituted by $C_1$–$C_4$-alkyl, $C_1$–$C_4$-alkoxy, OH, halogen or $CF_3$;

or a tautomer or pharmaceutically acceptable salt thereof.

9. A compound of the formula (II) according to claim 8, wherein:

$R^3$ denotes $C_1$–$C_4$-alkyl, which is substituted by a group selected from the group consisting of —C(=NOH)$NH_2$, —C(=NCOO—$C_1$–$C_6$-alkyl)$NH_2$ and –C(=NCOO—$C_1$–$C_6$-alkyl-phenyl)$NH_2$; and, $R^7$ denotes hydroxy, —COO—$C_1$–$C_6$-alkyl, —CO-phenyl, —CO-pyridyl or —COO—$C_1$–$C_6$-alkyl-phenyl, whilst in the abovementioned group the phenyl ring may be substituted by $C_1$–$C_4$-alkyl, $C_1$–$C_4$-alkoxy, OH, halogen or $CF_3$, or a tautomer or pharmaceutically acceptable salt thereof.

10. A compound of the formula (II) according to claim 9, wherein:

$R^7$ denotes hydroxy, methoxycarbonyl, ethoxycarbonyl, propyloxycarbonyl, butyloxycarbonyl, benzoyl, benzyloxycarbonyl or nicotinoyl, or a tautomer or pharmaceutically acceptable salt thereof.

11. A compound of the formula (III)

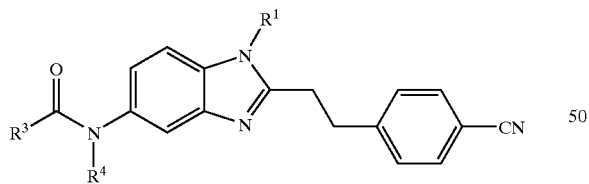

(III)

wherein:

$R^1$ denotes a group selected from the group consisting of $C_1$–$C_6$-alkyl, $C_2$–$C_6$-alkenyl and $C_2$–$C_6$-alkynyl, which is optionally mono-, di- or trisubstituted by one or more of the groups hydroxy, $C_1$–$C_4$-alkoxy, $CF_3$, phenoxy, COOH, halogen, —CO($C_1$–$C_4$-alkoxy), —CO—$NR^5R^6$, —$NR^5R^6$ or $C_1$–$C_4$-alkoxy-phenoxy, or phenyl-$C_1$–$C_4$-alkyl, which is optionally mono-, di- or trisubstituted by one or more of the groups hydroxy, $C_1$–$C_4$-alkoxy, carboxy, halogen, $C_1$–$C_4$-alkoxycarbonyl or $CF_3$, or a 5- or 6-membered, saturated or unsaturated heterocycle linked directly or via a $C_1$–$C_4$-alkylene bridge, which may contain one or two heteroatoms selected from the group consisting of oxygen, nitrogen and sulphur and which is optionally substituted by $C_1$–$C_4$-alkyl or benzyl;

$R^3$ denotes a $C_1$–$C_6$-alkyl, $C_1$–$C_6$-hydroxyalkyl or $C_1$–$C_4$-alkoxy-$C_1$–$C_4$-alkyl group which may be mono- or disubstituted by one, two or three of the groups —$NR^5R^6$, —C(=NH)$NH_2$ or —NH—C(=NH)$NH_2$, or a 5-, 6- or 7-membered, saturated or unsaturated heterocycle linked directly or via a $C_1$–$C_4$-alkylene bridge or a $C_2$–$C_4$-alkenylene bridge, which may contain one, two or three heteroatoms selected from the group consisting of oxygen, nitrogen and sulphur and which is optionally mono- or disubstituted by hydroxy, $C_1$–$C_4$-alkyl, —COO—$C_1$–$C_4$-alkyl, —$CONH_2$, benzyl, diphenylmethyl, phenyl or pyridylmethyl, pyridyl, and wherein the phenyl substituent may be mono-, di- or trisubstituted by one or more groups selected from the group consisting of $C_1$–$C_4$-alkyl, $C_1$–$C_4$-alkoxy, halogen, $C_1$–$C_4$-alkyl-halogen and —$NH_2$, cyclopropyl, cyclobutyl, cyclopentyl or cyclohexyl, each of which may be mono- or disubstituted by one or two of the groups —$NR^5R^6$, —C(=NH)$NH_2$ or —NH—C(=NH)$NH_2$, or phenyl-$C_1$–$C_4$-alkyl or naphthyl-$C_1$–$C_4$-alkyl, which is optionally substituted at the alkylene bridge by —$NR^5R^6$ and may be mono- or disubstituted at the phenyl ring by one or two of the groups —$NO_2$, —$NR^5R^6$, —$C_1$–$C_4$-alkyl-$NR^5R^6$, —C(=NH)$NH_2$ or —NH—C(=NH)$NH_2$;

$R^4$ denotes $C_1$–$C_6$-alkyl, which is mono- or disubstituted by one or two groups selected from the group consisting of furanyl, benzofuranyl, thiophenyl, benzothiophenyl, anthracenyl, phenyl, pyridyl and naphthyl, while the substituents phenyl and naphthyl may in turn be mono-, di- or trisubstituted by one or more of the groups selected from the group consisting of $C_1$–$C_4$-alkyl, $C_1$–$C_4$-alkoxy, halogen, $C_1$–$C_4$-alkyl-halogen, —$NH_2$, —$NH(C_1$–$C_4$-alkyl), —$N(C_1$–$C_4$-alkyl)$_2$, $NO_2$, hydroxy, —$CF_3$, —NHCO—$C_1$–$C_4$-alkyl, —COOH, —COO($C_1$–$C_4$-alkyl), —$CONH_2$, —CONH($C_1$–$C_4$-alkyl), —CON($C_1$–$C_4$-alkyl)$_2$, —CONH($C_1$–$C_4$-alkyl)-COO($C_1$–$C_4$-alkyl) and phenyl-$C_1$–$C_6$-alkyl; and, $R^5$ and $R^6$, which may be identical or different, denote hydrogen, $C_1$–$C_4$-alkyl, phenyl, pyridyl or benzyl, which is optionally substituted by a group selected from the group consisting of halogen, halo-$C_1$–$C_4$-alkyl, —OH, $C_1$–$C_4$-alkyl, —O—$C_1$–$C_4$-alkyl, —CO—O—$C_1$–$C_4$-alkyl, —$NO_2$, phenyl, pyrrolidin-1-yl, piperidin-1-yl, —$NH_2$, —NH—$C_1$–$C_4$-alkyl, —N($C_1$–$C_4$-alkyl)$_2$ and —C(=NH)$NH_2$—$NH_2$, or a tautomer or salt thereof.

12. A compound of the formula (III) according to claim 11 wherein:

$R^1$ denotes $C_1$–$C_6$-alkyl, which is optionally mono-, di- or trisubstituted by one or more of the groups hydroxy, $C_1$–$C_4$-alkoxy, $CF_3$, phenoxy, COOH, halogen, —CO($C_1$–$C_4$-alkoxy), —CO—$NR^5R^6$, —$NR^5R^6$ or $C_1$–$C_4$-alkoxy-phenoxy, or $R^3$ denotes a $C_1$–$C_6$-alkyl group, which may be mono- or disubstituted by one or two of the groups —$NR^5R^6$, —C(=NH)$NH_2$ or —NH—C(=NH)$NH_2$, or a 5-, 6- or 7-membered, saturated or unsaturated heterocycle linked directly or via a $C_1$–$C_4$-alkylene bridge, which may contain one, two or three heteroatoms selected from the group consisting of oxygen, nitrogen and sulphur and is optionally mono- or disubstituted by hydroxy, $C_1$–$C_4$-alkyl, benzyl, phenyl or pyridyl, and wherein the phenyl substituent may be substituted by one of the groups selected from the group consisting of $C_1$–$C_3$-alkyl, $C_1$–$C_3$-alkoxy, halogen, trifluoromethyl and $NH_2$, cyclopropyl, cyclopentyl or cyclohexyl, each of which may be mono- or disubstituted by one or two of the groups —$NR^5R^6$, —C(=NH)$NH_2$ or —NH—C(=NH)$NH_2$, or phenyl-$C_1$–$C_4$-alkyl or naphthyl-$C_1$–$C_4$-alkyl, which is optionally substituted by —$NR^5R^6$ at the alkylene bridge and may be mono- or disubstituted at the phenyl ring by one or two of the groups —$NO_2$, —$NR^5R^6$, —$C_1$–$C_4$-Alkyl-$NR^5R^6$, —C(=NH)$NH_2$ or —NH—C(=NH)$NH_2$, $R^4$ denotes $C_1$–$C_6$-alkyl, which is mono- or disubstituted by one or two groups selected from the group consisting of phenyl, pyridyl and naphthyl, wherein the substituents phenyl and naphthyl may in turn be substituted by one of the groups selected from the group consisting of $C_1$–$C_4$-alkyl, $C_1$–$C_4$-alkoxy, halogen, —$C_1$–$C_4$-alkyl-halogen, —$NH_2$; and $R^5$ and $R^6$, which may be identical or different, denote hydrogen, $C_1$–$C_4$-alkyl, pyridyl or benzyl, which is optionally substituted by a group selected from the group consisting of —OH, —O—$C_1$–$C_3$-alkyl, —$NO_2$, phenyl, pyrrolidin-1-yl, —$NH_2$, —NH—$C_1$–$C_4$-alkyl, —N($C_1$–$C_4$-alkyl)$_2$ and —C(=NH)$NH_2$, or a tautomer or salt thereof.

13. A compound of the formula (III) according to claim 11 wherein:

$R^1$ denotes $C_1$–$C_4$-alkyl, which is optionally mono-, di- or trisubstituted by one or more of the groups hydroxy, $C_1$–$C_4$-alkoxy, $CF_3$, phenoxy, COOH, halogen, —CO($C_1$–$C_4$-alkoxy), —CO—$NR^5R^6$, —$NR^5R^6$ or $C_1$–$C_4$-alkoxy-phenoxy, or $R^3$ denotes a $C_1$–$C_4$-alkyl group, which may be mono- or disubstituted by one or two of the groups —$NR^5R^6$, —C(=NH)$NH_2$ or —NH—C(=NH)$NH_2$, or a 5-, 6- or 7-membered, saturated or unsaturated heterocycle linked directly or via a methylene or ethylene bridge, which may contain one or two heteroatoms selected from the group consisting of oxygen and nitrogen and is optionally substituted by methyl or benzyl;

naphthylmethyl, benzyl or phenylethyl, which is optionally substituted by —$NR^5R^6$ at the alkylene bridge and may be substituted at the phenyl ring by a group selected from the group consisting of —$NR^5R^6$, —$C_1$–$C_4$-alkyl-$NR^5R^6$, —C(=NH)$NH_2$ and —NH—C(=NH)$NH_2$, $R^4$ denotes $C_1$–$C_5$-alkyl, which is mono- or disubstituted by one or two groups selected from the group consisting of phenyl, pyridyl and naphthyl; and, $R^5$ and $R^6$, which may be identical or different, denote hydrogen, methyl, ethyl, propyl, butyl, pyridyl or benzyl, which is optionally substituted by a group selected from the group consisting of —OH, methoxy, —$NO_2$, phenyl, pyrrolidin-1-yl, —$NH_2$, —NH-methyl, —N(methyl)$_2$, —NH-ethyl, —N(ethyl)$_2$ and —C(=NH)$NH_2$, or a tautomer or salt thereof.

14. A compound of the formula (III) according to claim 11 wherein:

$R^1$ denotes methyl, ethyl, propyl or butyl;

$R^3$ denotes a $C_2$–$C_4$-alkyl group, which may be mono- or disubstituted by one or two of the groups —$NR^5R^6$, —C(=NH)$NH_2$ or —NH—C(=NH)$NH_2$, or a 6-membered, saturated or unsaturated heterocycle linked via a methylene or ethylene bridge, which contains one or two nitrogen atoms and is optionally substituted by methyl or benzyl;

naphthylmethyl, benzyl or phenylethyl, which is optionally substituted by —$NR^5R^6$ at the alkylene bridge and which are substituted at the phenyl ring by a group selected from the group consisting of —$NR^5R^6$, —$C_1$–$C_4$-alkyl-$NR^5R^6$, —C(=NH)$NH_2$ and —NH—C(=NH)$NH_2$, $R^4$ denotes an alkyl group selected from the group consisting of methyl, ethyl, propyl, butyl and pentyl, which is mono- or disubstituted by one or two groups selected from the group consisting of phenyl, pyridyl and naphthyl; and, $R^5$ and $R^6$, which may be identical or different, denote hydrogen, methyl, ethyl, propyl, butyl, pyridyl or benzyl, which is optionally substituted by a group selected from the group consisting of —OH, methoxy, —$NO_2$, phenyl, pyrrolidin-1-yl, —$NH_2$, —NH-methyl, —N(methyl)$_2$ and —C(=NH) $NH_2$, or a tautomer or salt thereof.

15. A compound of the formula (III) according to claim 11 wherein:

$R^1$ denotes methyl, ethyl or propyl;

$R^3$ denotes methyl which is substituted by a group selected from the group consisting of pyridylamino, benzylamino, N-benzyl-N-methylamino, N-(amidinobenzyl)amino, N-(amidinobenzyl)-N-methyl-amino, N-(dimethylaminobenzyl)amino, (pyrrolidin-1-ylbenzyl)amino and N-(dimethylaminobenzyl)-N-methyl-amino, or an alkyl group selected from the group consisting of ethyl and propyl, which may be mono- or disubstituted by one or two groups selected from the group consisting of —$NH_2$ and —NH—C(=NH)$NH_2$, or a heterocycle linked via an ethylene bridge, selected from the group consisting of piperidine, morpholine and piperazine, which is optionally substituted by methyl, benzyl or diphenylmethyl;

phenylethyl, which is optionally substituted by —$NH_2$ at the ethylene bridge and is substituted at the phenyl ring by a group selected from the group consisting of pyrrolidin-1-yl, —$NH_2$, —N(methyl)$_2$, —$CH_2$—$NH_2$ and —C(=NH)$NH_2$; and, $R^4$ denotes benzyl, pyridylmethyl, naphthalinylmethyl or diphenylpropyl, or a tautomer or salt thereof.

16. A compound of the formula (III) according to claim 11 wherein:

$R^1$ denotes methyl, ethyl or propyl;

$R^3$ denotes methyl, which is substituted by a group selected from the group consisting of N-(amidinobenzyl)amino, N-(amidinobenzyl)-N-methyl-amino, N-(dimethylaminobenzyl)amino, (pyrrolidin-1-ylbenzyl)amino and N-(dimethylaminobenzyl)-N-methyl-amino, or a piperidine or piperazine linked via an ethylene bridge, which is optionally substituted by benzyl;

phenylethyl, which is optionally substituted by —NH$_2$ at the ethylene bridge and is substituted by —C(=NH)NH$_2$ at the phenyl ring; and, R$^4$ denotes benzyl, naphthalinylmethyl or diphenylpropyl, or a tautomer or salt thereof.

17. A method for treating bronchial asthma, allergic rhinitis, allergic conjunctivitis, atopic dermatitis, urticaria, allergic otitis, an allergic gastro-intestinal disorder, Crohn's disease, ulcerative colitis, anaphylactic shock, septic shock, shock lung (ARDS) or arthritis which comprises administering to a host suffering from one of said conditions a therapeutic amount of a compound of the formula I, in accordance with claim 1, 2, 3, 4, 5 or 6, a compound of the formula IA, in accordance with claim 7, or a compound of the formula II, in accordance with claim 8, 9 or 10.

18. A pharmaceutical composition comprising a compound of the formula I, in accordance with claim 1, 2, 3, 4, 5 or 6, a compound of the formula IA, in accordance with claim 7, or a compound of the formula II, in accordance with claim 8, 9 or 10, and a pharmaceutically acceptable carrier.

\* \* \* \* \*